(12) United States Patent
Thies

(10) Patent No.: US 11,529,135 B2
(45) Date of Patent: Dec. 20, 2022

(54) BONE ANCHOR DELIVERY SYSTEM DEVICE AND METHOD WITH IMPROVED HANDLE

(71) Applicant: Maruho Medical, Inc., Marietta, GA (US)

(72) Inventor: Brendan D. Thies, Woodstock, GA (US)

(73) Assignee: Maruho Medical, Inc., Marietta, GA (US)

( * ) Notice: Subject to any disclaimer, the term of this patent is extended or adjusted under 35 U.S.C. 154(b) by 399 days.

(21) Appl. No.: 16/986,454

(22) Filed: Aug. 6, 2020

(65) Prior Publication Data

US 2022/0039789 A1 Feb. 10, 2022

(51) Int. Cl.
*A61B 17/04* (2006.01)
*A61B 17/16* (2006.01)
*A61B 17/00* (2006.01)

(52) U.S. Cl.
CPC ...... *A61B 17/0401* (2013.01); *A61B 17/1604* (2013.01); *A61B 17/1633* (2013.01); *A61B 2017/00424* (2013.01); *A61B 2017/044* (2013.01); *A61B 2017/0409* (2013.01); *A61B 2017/0445* (2013.01)

(58) Field of Classification Search
CPC ............ A61B 17/0401; A61B 2017/0409
See application file for complete search history.

(56) References Cited

U.S. PATENT DOCUMENTS

| 8,845,685 | B2 | 9/2014 | Stone et al. |
| 9,241,703 | B2 | 1/2016 | Lanois et al. |
| 9,241,705 | B2 | 1/2016 | Lanois et al. |
| 9,247,933 | B2 | 2/2016 | Lanois et al. |
| 9,271,717 | B2 | 3/2016 | Lanois et al. |
| 9,936,940 | B2 | 4/2018 | Palese et al. |
| 10,335,137 | B2 | 7/2019 | Arai et al. |
| 10,582,919 | B2 | 3/2020 | Hirotsuka et al. |
| 10,631,843 | B2 | 4/2020 | Stone et al. |
| 10,722,343 | B2 * | 7/2020 | Pilgeram ............... A61F 2/0811 |
| 2008/0275431 | A1 * | 11/2008 | Stone ................. A61B 17/0401 606/1 |
| 2009/0234387 | A1 * | 9/2009 | Miller ................ A61B 17/0401 606/232 |
| 2010/0105979 | A1 * | 4/2010 | Hamel ............... A61B 17/0401 600/30 |

(Continued)

*Primary Examiner* — Nicholas W Woodall
(74) *Attorney, Agent, or Firm* — David L. King

(57) ABSTRACT

A bone anchor delivery system device (10) has a retractable punch driver assembly and a locking mechanism (32). The punch driver assembly has a retractable punch shaft (30) and a guide (20) for receiving the retractable punch shaft (30). The guide (20) is rotatable relative to the punch shaft (30) and the shaft has an extended length with bone penetrating tip (35) at a first end (33). The locking mechanism (32) for locking the retractable punch shaft (30) from linear movement and rotational movement relative to the guide (20) is positioned at an opposite second end. The retractable punch shaft (30) has a reduced diameter end (33) extending from the tip (35) toward a shoulder stop for receiving a releasable punch (12). The releasable punch (12) has a hollow opening for receiving the reduced diameter end (33) of the punch shaft (30). The punch (12) is profiled to pierce and form a bone anchor hole.

34 Claims, 29 Drawing Sheets

(56) References Cited

U.S. PATENT DOCUMENTS

2010/0179873 A1* 7/2010 Li .................. G06Q 30/0241
 705/14.49
2014/0277129 A1 9/2014 Arai et al.

* cited by examiner

BONE ANCHOR DELIVERY SYSTEM DEVICE AND METHOD WITH IMPROVED HANDLE

TECHNICAL FIELD

The present invention relates to methods and instruments for fixation of sutures and tissue to bone, more particularly to a bone anchor system for securing sutures for attachment of soft tissue like ligament and cartilage to bone.

BACKGROUND OF THE INVENTION

The use of bone screw anchors to hold sutures is a widely accepted practice in shoulder or knee repair and fixation of soft tissue such as ligaments, cartilage and tendons to bone. Ideally the suture anchor is easy to install and provides a solid reliable way to fix the sutures to the bone. The bone has a hard outer cortical shell with a softer underlying region of cancellous bone tissue. The anchor must hold sutures after thousands of repetitive motions tensioning and relaxation until the ligament or tendon repair has time to heal and secure itself to the bone and muscle tissue.

Older style bone anchors had an external eyelet to allow the sutures to be fed through after the screw was driven into the bone. This left the eyelet exposed in the soft muscle tissue.

Later versions of bone anchors have the sutures inserted inside the screw tip well inside the bone. This allows the screw outer end to stay flush with the cortical bone outer surface. The sutures can pass inside in some hollow screws from the tip to the outer surface. Others have the sutures held at the tip end and are exterior held between the anchor screw threads and the bone. In some suture anchor systems there is a self-driving feature that has a stainless steel punch with a steel tip that can be malleted into the bone. This design leaves the tip end trapped in the bone opening meaning the patient has a small steel tip in his shoulder or knee.

Ideally the procedure should insure the bone anchor is easily installed leaving no punch tip fragments in the body and more particularly avoiding having steel tips or metal fragments left in the bone. These issues were addressed in U.S. Pat. No. 9,247,933 B2 entitled "Bone Anchor Delivery System and Method" which is being incorporated by reference herein in its entirety. The present invention utilizes all of the beneficial features of that device, but with a greatly improved ergonomically better handle design. One of the objectives of the present invention is to streamline the operation of the device by incorporating the features internally concealed in the handle in a unique and novel construction as described herein.

The present invention provides a threaded bone anchor that is easy to install wherein the sutures are held without leaving metal fragments or metal tips and, furthermore, this is accomplished with a unique insertion tool and anchor screw assembly to make the procedure simple and convenient to use.

SUMMARY OF THE INVENTION

A bone anchor delivery system device has a retractable punch driver assembly and a multi-piece handle assembly. The punch driver assembly has a retractable punch shaft and a guide for receiving the retractable punch shaft. The guide being rotatable relative to the punch shaft and the shaft having an extended length with bone penetrating tip at a first end, and a bent end for locking the retractable punch shaft from linear movement and rotational movement relative to the guide at an opposite second end. The multi-piece handle assembly has a leading handle rotatable about the guide and a middle handle portion fixed to the guide and a locking knob configured to prevent linear movement of the retractable punch. The middle handle is rotatable independent of said lower portion. The middle handle has a slot to receive the bent end to allow linear movement of the retractable punch shaft. The punch shaft is a rod or wire and the bent end is integrally formed as part of the rod or wire at the second end by a bending of the punch shaft to fit into the slot of the middle handle and a cylinder of the locking knob has an end locking the punch shaft in place linearly.

The bent end of the shaft is L shaped at the second end. The middle handle has two longitudinal halves. Each half has a leading end and a trailing end. Each end has a semicircular opening and when the halves are joined the openings form a circular opening. The leading end is configured to rotatably hold the leading handle and the trailing end opening is configured to receive the locking knob.

The bent end of the shaft, when placed in a first half of the middle handle, lies in between two ribs. The ribs extend longitudinally forming the slot for allowing linear movement. The leading handle has a pair of appendages for wrapping lengths of sutures about. The locking knob has a bump aligned with the trailing end opening of the open end of the middle handle. The open end has a pair of linear extending protrusions. A first protrusion is at a locked position. The second protrusion is at an unlocked position. When the bump passes each protrusion, as the locking knob rotates relative to the middle handle, a tactile feel indication occurs.

The locking knob moves from the lock position to the unlock position by a quarter turn rotation. The rotation of the locking knob to the unlock position couples the middle handle and the locking knob so rotation of either rotates both. The quarter turn rotation to the unlock position is directionally clockwise. Continued rotation clockwise threads the anchor in bone as the shaft moves towards a retracted position in the channel.

The retractable punch shaft has a reduced diameter end extending from the tip toward a shoulder stop for receiving a releasable punch. The releasable punch has a hollow opening for receiving the reduced diameter end and bone penetration tip at the first end profiled to be complimentary to the tip and an opposite second end for abutting the shoulder stop of the punch shaft.

Preferably, the reduced diameter end of the punch shaft and the punch have a snap lock feature to hold the punch. The snap lock feature allows for rotational movement of the punch relative to the punch shaft. The releasable punch has a plurality of openings for threading one or more sutures. In one embodiment, the releasable punch openings are one or more pairs of slots sized to receive a plurality of sutures.

The bone anchor delivery system device further has a releasable threaded bone anchor. The threaded bone anchor is hollow having an opening attachment onto the guide. The bone anchor extends from a first leading end to an opposite second end abutting the guide. The guide has a reduced end having a releasable snap locking feature and the bone anchor has a complimentary releasable lock for holding the bone anchor to the guide. The bone anchor delivery system device has the punch shaft extending past the guide to the shoulder second end by a length L, wherein L is equal to the length of the bone anchor. In the use of the anchor delivery system device, the punch end tip penetrates the bone creating an opening or hole extending to a depth wherein the bone anchor is positioned adjacent above the bone opening and thereafter threaded into the bone opening or hole.

Preferably, the punch and the bone anchor are non-metal. The bone anchor or the punch can be made of synthetic or natural non-metal material. Either can be made of a plastic material, the plastic material is preferably PEEK. The punch or bone anchor also can be made of a bioabsorbable material. The bone anchor can be made of cortical bone.

Definitions

As used in this specification, the singular forms "a," "an" and "the" include plural referents unless the context clearly dictates otherwise. Thus, for example, the term "a material" is intended to mean one or more materials, or a combination thereof.

BRIEF DESCRIPTION OF THE DRAWINGS

The invention will be described by way of example and with reference to the accompanying drawings in which:

FIG. 27A shows the step of locating the insertion position.

FIG. 27B shows the step of driving the punch to depth.

FIG. 27C shows the steps of releasing the lock mechanism and driving the anchor by rotation of the device until flush with the bone surface.

FIG. 27D shows the step of pulling back the device to release it from the bone anchor.

DETAILED DESCRIPTION OF THE INVENTION

Figure 1:
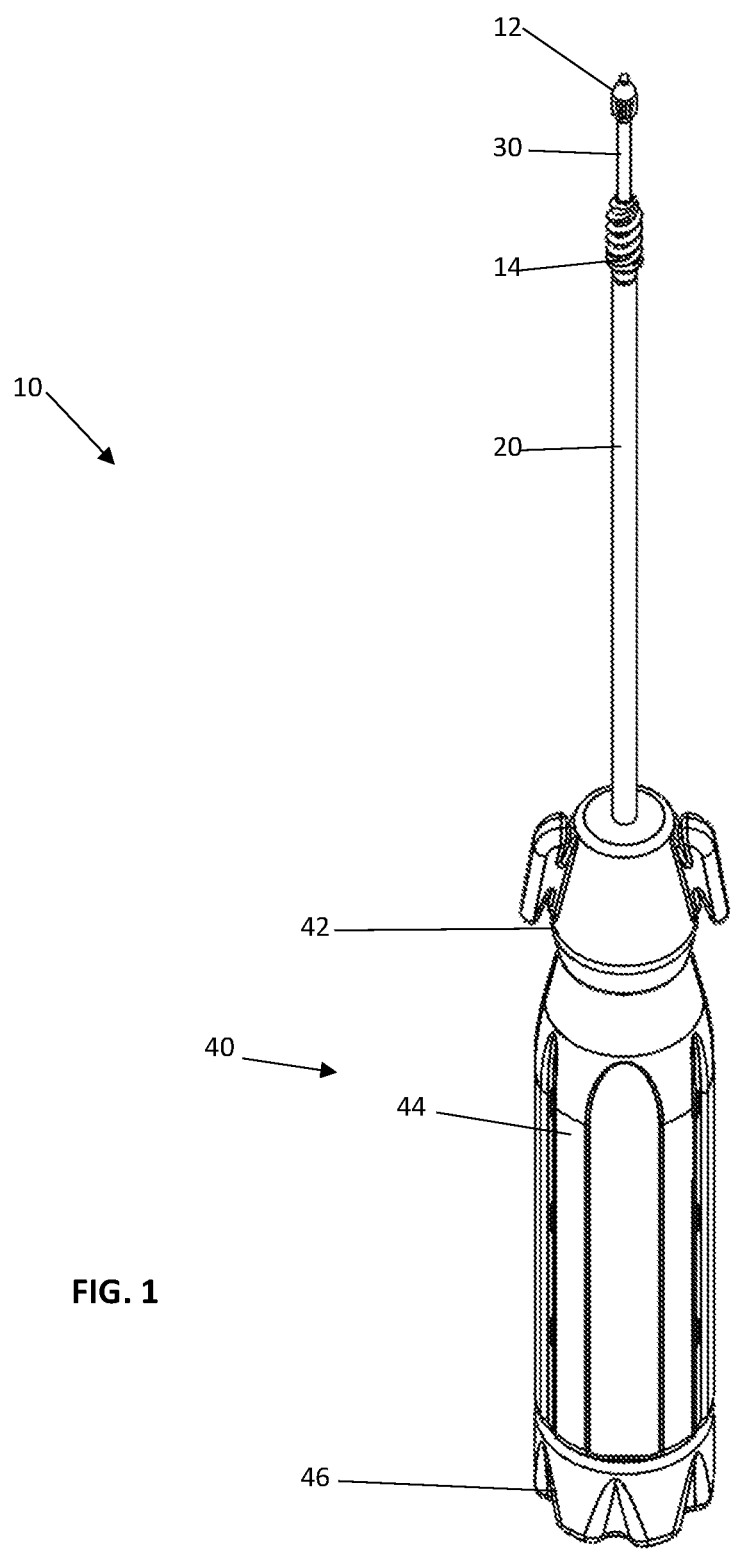
FIG. 1 shows a perspective view of the bone anchor delivery system device of the present invention.
Figure 2:
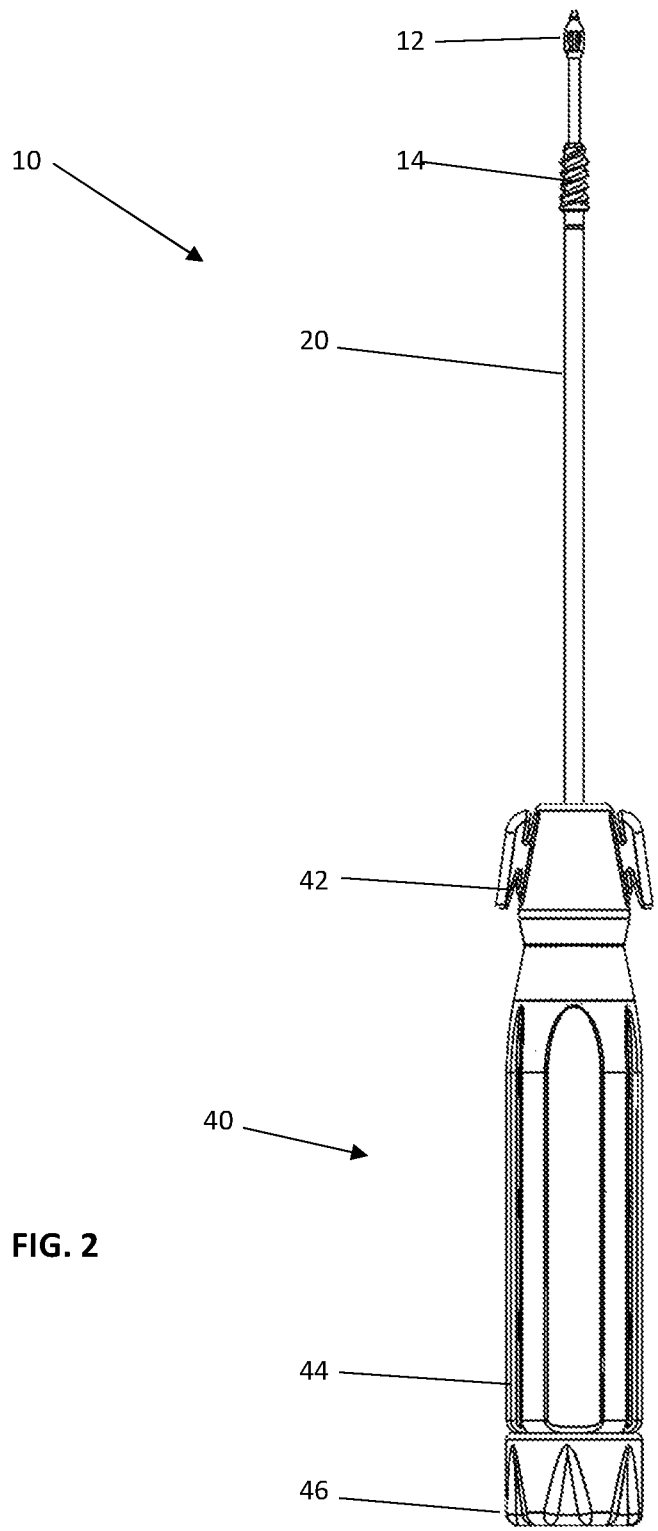
FIG. 2 is a side plan view of the device of FIG. 1.
Figure 5:
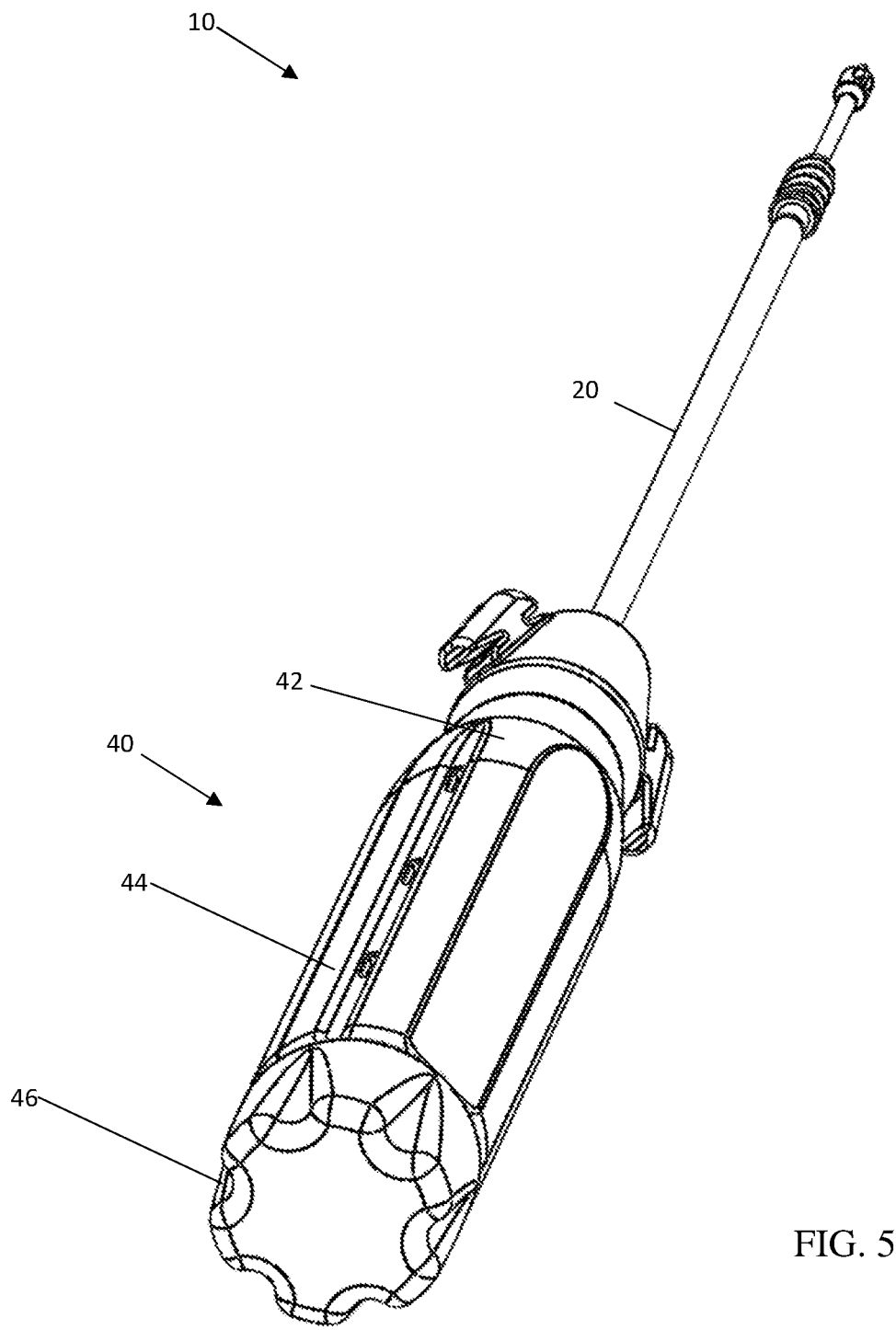
FIG. 5 is a second perspective view of the device from a trailing end perspective.

With reference to FIGS. 1 and 5, perspective views and FIG. 2, a plan view; of a bone anchor delivery system device 10 is illustrated. As further shown in FIGS. 1, 2 and 5, the device 10, as illustrated, has a multi-part handle 40, a leading handle 42 which is rotatable about a guide 20, a middle handle 44 which is fixed to the guide 20, and a rotatable locking knob 46. As further illustrated in FIG. 1, the guide 20 extends from the handle 40 located at a second end to a leading first end. The guide 20, as illustrated, is hollow and has a punch shaft 30 extending from inside the guide 20 to the leading first end. At the very tip 35 of the leading first end 33 of the guide 20 is illustrated a releasable punch 12. Extending further up the punch shaft 30 is illustrated a bone anchor 14. The bone anchor 14 preferably has a length that is approximately equal to the length of that part of the shaft 30 extending beyond the guide 20, as illustrated. The bone anchor 14 preferably is a threaded screw structure hollow on the inside which allows the punch shaft 30 to extend through the bone anchor 14, as illustrated.

At the handle 40, the guide 20 is shown extending partially into a slotted opening 41 of the middle handle 44 as illustrated in FIGS. 6A-8. The punch shaft 30 extends beyond the guide 20 and is bent forming an L shaped end inside the handle 44 as illustrated. This punch shaft 30 extends from the slot 41 upwardly and at the bent end 38 is blocked by ribs 43, 45 in the middle handle 44 and a rotatable cylinder 60 with a channel 62. The rotatable cylinder 60 is shown in the locked position. This bent end 38 forms a stop mechanism that abuts into ribs 43 and 45 in the middle handle 44. This prevents the punch shaft 30 from moving linearly or rotating relative to the device 10. As further shown, the middle handle portion 44 has a rounded somewhat flattened open end 44C. This flattened open end 44C receives the locking knob 46 above the middle handle 44. This locking knob 46 has a flat end 46A which provides a surface on which a surgeon may take a mallet and drive the device into bone.

Figure 3A:
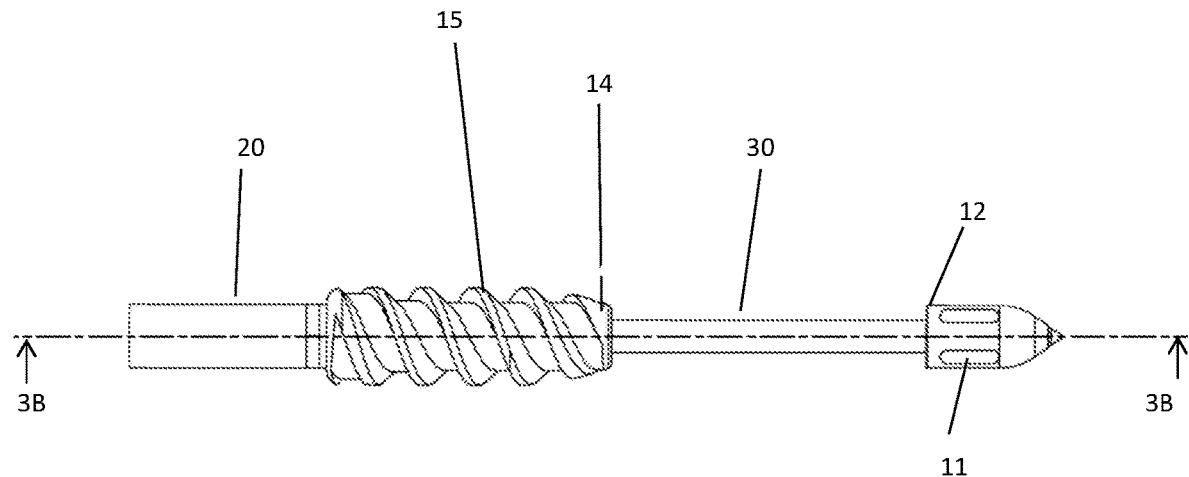
FIG. 3A is an enlarged side view of the leading end portion of the device.
Figure 3B:
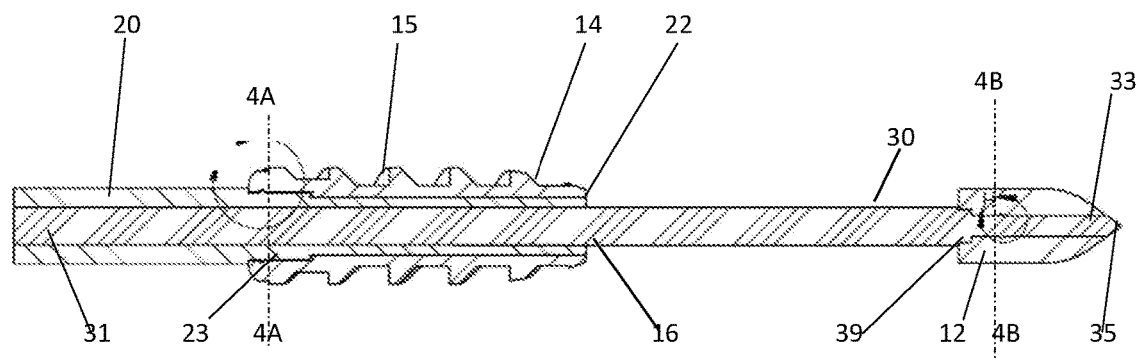
FIG. 3B is a cross sectional view of the leading end portion of the device taken along lines 3B-3B of FIG. 3A.
Figure 6A:
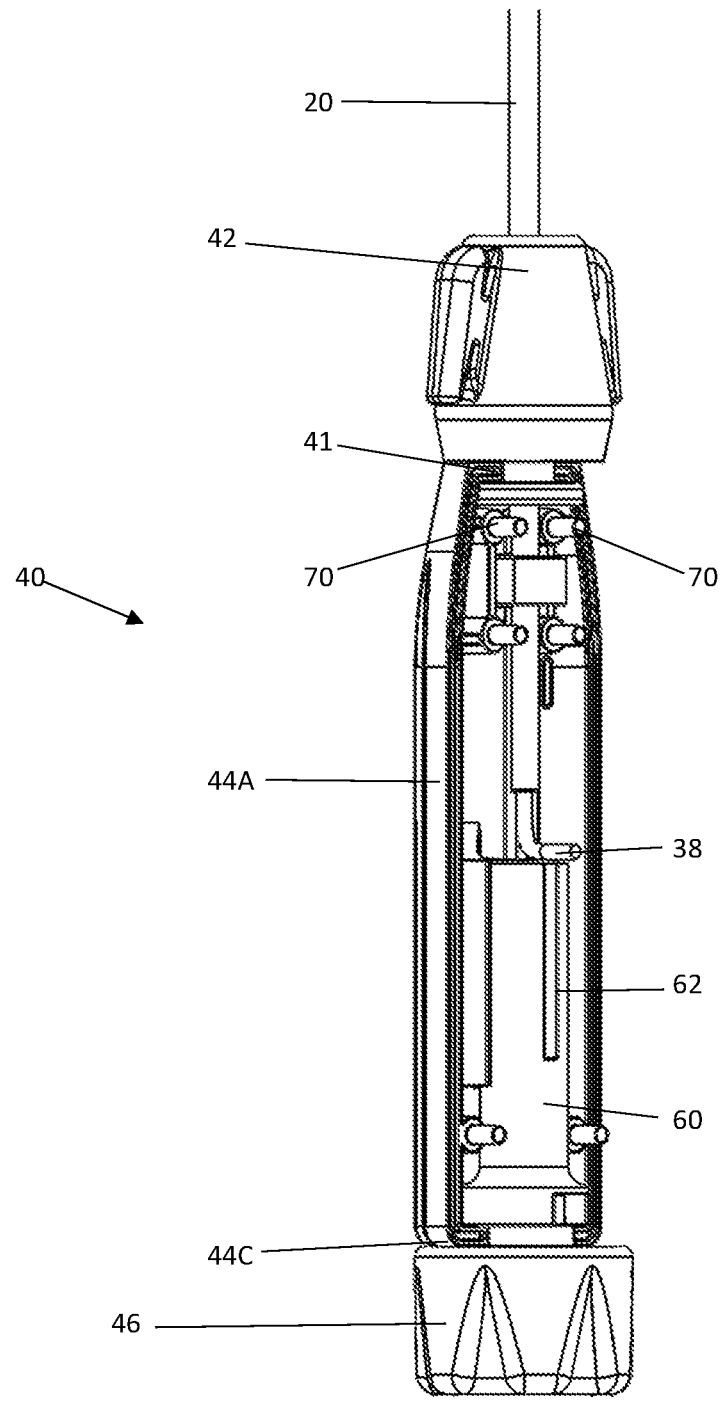
FIG. 6A is a partial view of the handle with half of the middle portion removed exposing the shaft trailing end in the extended and locked orientation.

The punch shaft 30 is best illustrated in the cross sectional view FIG. 3B wherein the punch shaft 30 is shown bent into the configuration making the stop mechanism bent end 38 that is easily held into position into the middle handle 44 as the handle 44 is formed into two longitudinally extending halves 44A and 44B and as illustrated in FIG. 6A. The shaft 30 is laying in half 44A. To release the punch shaft 30 from the ribs 43 and 45 holding locking knob 46, the surgeon simply rotates the knob 46 as illustrated in the various figures which will align the bent end 38 of the shaft 30 with the channel 62 and allow the punch shaft 30 to slide into the slot or channel 62, when this occurs the punch shaft 30 is free to move linearly up or down relative to the guide 20 and middle handle 44.

With reference to FIGS. 3A, 3B, 4A and 4B, the leading end 42 of the retractable punch driver assembly is illustrated. The retractable punch driver assembly comprises the guide 20 which is a hollow cylindrical tube into which the punch shaft 30 fits and extends from the bent end 38 through the guide 20 and extends beyond the guide 20 by a distance L. This distance L preferably extends sufficiently that the threaded bone anchor 14 fitted over an end 22 of the guide 20 as illustrated occupies approximately the same distance L between the end of the punch 12 and the guide 20. By providing the threaded bone anchor 14 of a length approximately equal to this extension of the punch shaft 30, it is possible to drive the punch 12 into the bone and leave the threaded bone anchor 14 above the bone surface. This enables the bone anchor 14 to be then rotationally driven into the bone opening created by the punch 12 once the device 10 has punched an opening into the bone. As shown in FIG. 3A, the punch 12 has a plurality of openings 11 to accept or receive sutures (not illustrated). As shown, these openings 11 can be slots to accommodate several sutures if so desired, preferably the sutures are threaded into and extend from one slot 11 inside the punch 12 through the other slot 11 to create a fixation of the suture within the punch 12, the ends of the suture being outside the device 10.

With reference to FIG. 3B, it is important to look at the punch 12 as it has a hollow opening for receiving the reduced diameter leading end 33 of the punch shaft 30. The end 33 of the punch shaft 30 is sharpened to a point at the tip 35 as illustrated. This reduced diameter end 33 preferably has a small ring 37 located between a shoulder 39 of the larger diameter portion 31 of the punch shaft 30 and the tip 35. This ring 37 as illustrated in FIG. 4B creates a snap locking feature. The punch 12 has a complimentary groove 13 that fits into the snap locking feature ring 37. As shown the punch 12 extends up to and abuts the larger diameter portion 31 of the punch shaft 30. On assembly, the snap feature ring 37 receives a groove 13 in the punch 12. Alternatively, a groove could be provided in the end 33 of the punch shaft 30 and a protrusion provided in the punch 12; however it is believed stronger that the punch 12 be provided with the groove 13 and the end 33 have a protrusion ring 37 on it. As illustrated, this ring 37 in connection with the groove 13 creates a releasable snap lock feature that enables the punch 12 to be placed over the tip 35 and end 33 snapped into position and held there. This prevents the punch 12 from slipping off inadvertently and is important that it be easily releasable once the punch 12 has been driven into the bone with the sutures in place in the slotted openings 11, as will be discussed later.

Figure 4A:
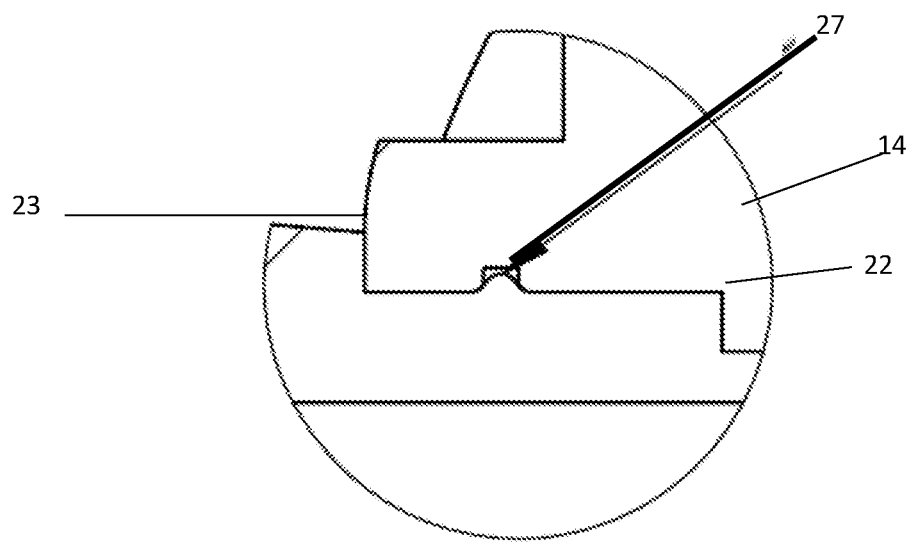
FIG. 4A is an enlarged view of the releasable snap retention feature of the threaded bone anchor and the guide taken from FIG. 3B.
Figure 4B:
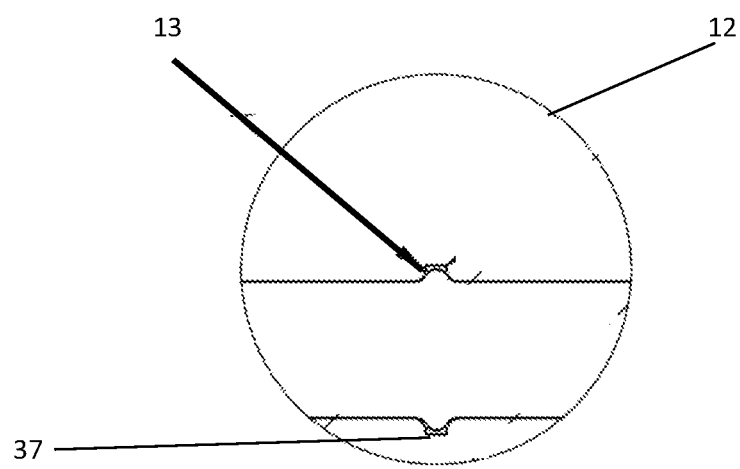
FIG. 4B is an enlarged view of the punch shaft tip releasable snap retention feature taken from FIG. 4A.

With reference to FIGS. 3B and 4A, the guide 20 extending over the punch shaft 30 has a one or more flat surfaces 22 at a leading or first end of the guide 20 and the bone anchor 14 similarly has one or more flat surfaces 16 complimentary to fit in a non-rotational fashion such that the bone anchor 14 is secured directly to the guide 20, preferably the guide 20 can be machined to a square and the anchor will have a square opening. The guide 20 further has a snap lock feature 27 at a reduced diameter end of the guide 20. This snap feature is a ring 27 similar to the snap feature 37 provided on the punch 12 and provides a protrusion or ring 27 around the reduced diameter portion 23 of the guide 20 that enables the bone anchor 14 to snap onto and be held there so that it is retained in this position as an assembly. This retention is releasable with a small amount of pressure enabling the bone anchor 14 to be released from the device 10 upon insertion into the bone. As shown, the bone anchor 14 preferably uses double helix tapered threads 15 that are sufficiently large to allow the bone anchor 14 to enter into the opening created by the punch 12 and to aggressively hold the anchor 14 into position in the cortical bone. It is important to note that the punch shaft 30 has an extended fixed distance that allows for punching the punch 12 a controlled depth leaving a length equal to the length L of the anchor 14. As discussed, it is important that the extension extend beyond the leading end of the bone anchor 14 by a distance at least equal to the total length of the bone anchor itself. Preferably, the tip 35 of the punch shaft 30 and the entire punch shaft 30 is made of stainless steel. The sharpened tip 35 assists in penetrating the bone along with the punch 12. It is preferable that the punch 12 and the bone anchor 14 be made of non-metal. Alternatively, while the anchor 14 and punch 12 could be made of metal, but it has been found that leaving remnants of metal in bone is not a preferred practice, and therefore, it is believed that a synthetic material such as plastic, preferably polyether ether ketone (PEEK) and or a bioabsorbable material would be preferred. The threaded bone anchor 14 itself may even include a bioabsorbable or natural material such as cortical bone. These and other possible materials are easily used in the manufacture of this device 10. It is even possible that natural compositions can be molded or cemented together in such a fashion that the punch itself can be made of a natural composition with the assistance of certain cements that would enable the punch 12 to be absorbed readily into the body, if so desired.

As shown, the punch 12 has a complimentary leading end that matches to the sharpened tip 35 of the end 33 such that upon hole penetration, the entire punch 12 has a diameter sufficient that it will allow the leading edge of the bone anchor 14 to engage the opening to initiate threading into the hole to secure the bone anchor 14 into the hole created by the punch 12.

Figure 27A:
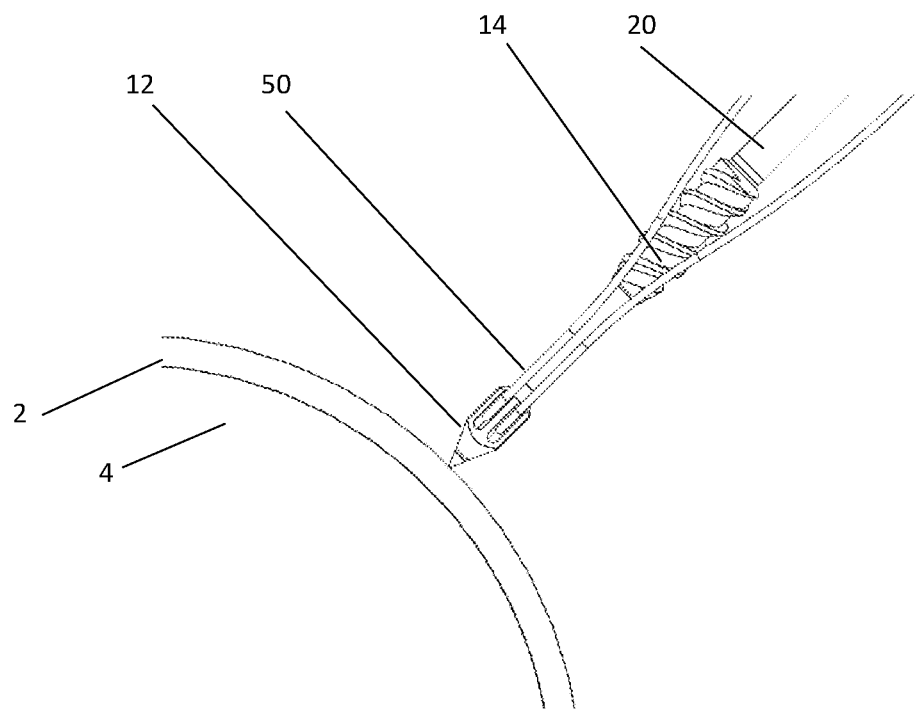
FIGS. 27A-27D illustrate the method of using the device to install the bone anchor of the present invention with sutures.
Figure 27B:
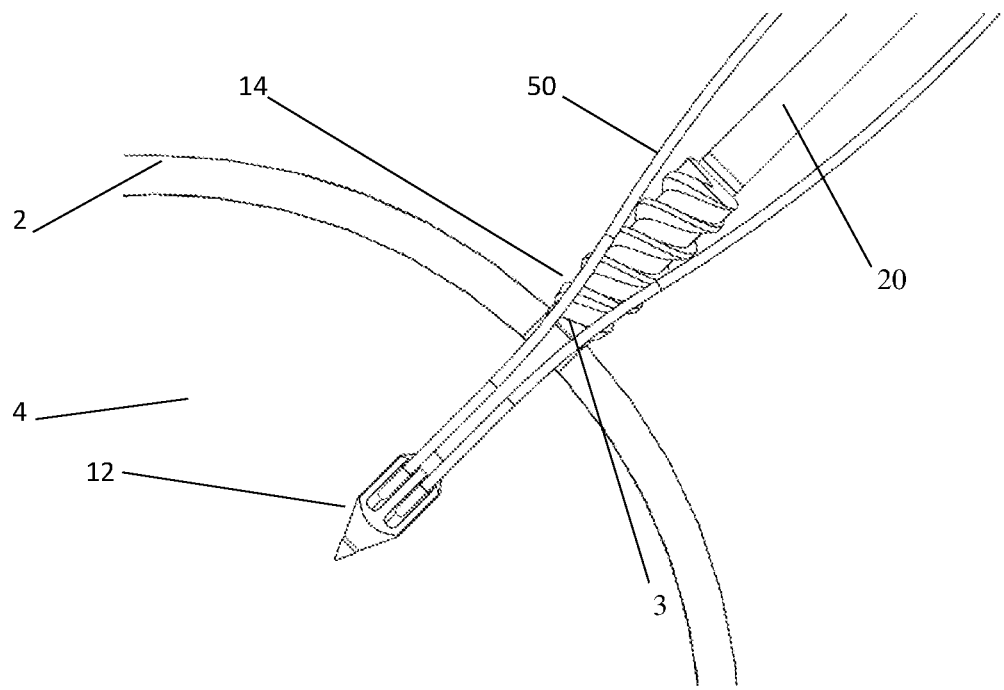
Figure 27C:
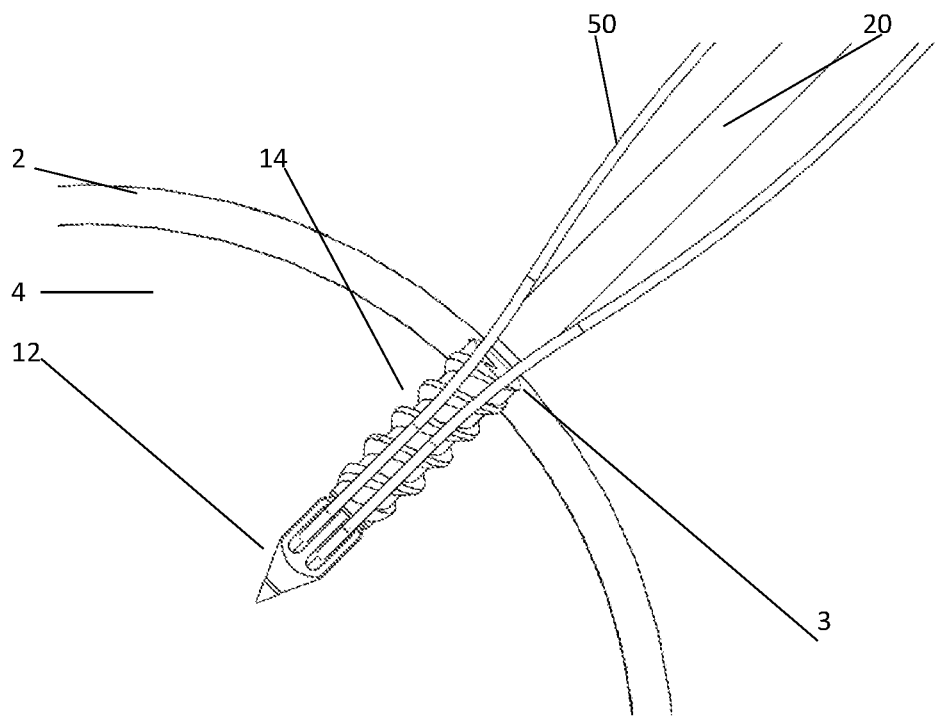
Figure 27D:
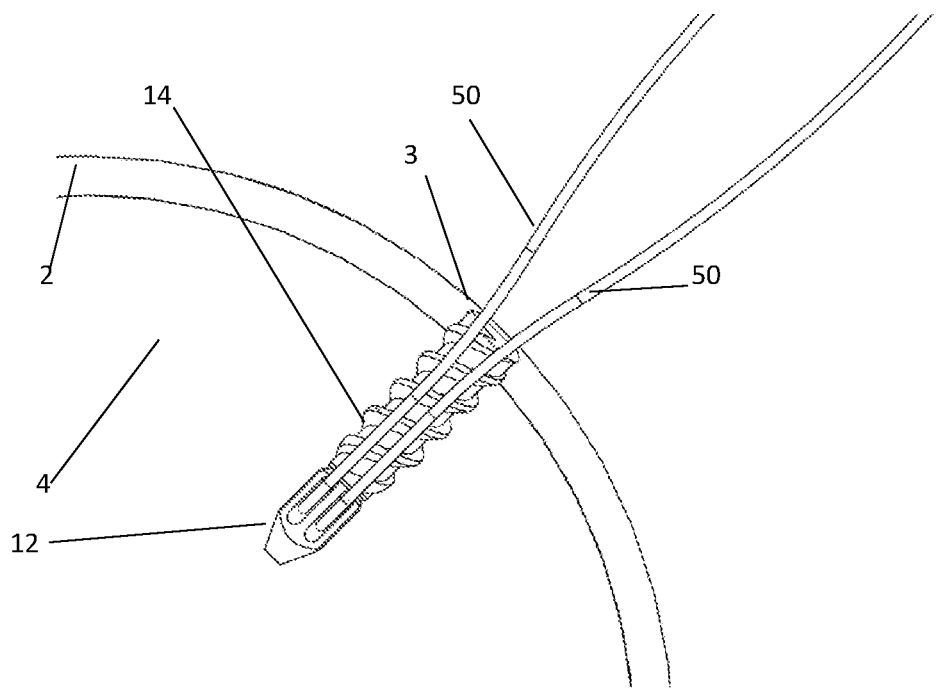

To better understand how the invention is used, reference is made to FIGS. 27A-27D. It is important to note that the surgeon should locate the position in which he wants the bone anchor 14 inserted. The bone anchor 14 with sutures 50 passed through slots 11 of the punch 12 will be positioned on the delivery device 10 and oriented in the desired direction the punch 12 is to penetrate into the bone 2. Once this position is secured, the surgeon can push and or use a mallet to punch to the desired depth. As shown in FIG. 27B, when the punch 12 achieves the desired depth, the anchor 14 is positioned directly above the opening at the outer surface of the cortical bone 2. The sutures 50 will be extending along the sides of the anchor 14, as illustrated. The sutures 50 can preferably be held off to one side or the other as they are retained in the punch 12 at the bottom of the hole 3 just created. The surgeon can then release the locked bent end of the punch shaft 30 by rotating the locking knob 46 by a ¼ turn and thereafter the shaft aligned in the channel 41 allows the shaft to move linearly as the knob 46 and rotate the middle handle 44 of the device 10 are coupled and rotate such that the bone anchor 14 can be threadingly engaged and driven into the opening 3 in cortical bone 2 and cancellous bone 4 until it is flush with the surface of the cortical bone 2. As the surgeon is rotating the device 10, the multi-part handle 40 provides an optimal way for the surgeon to hold the lower handle 42 stationary as it free to rotate relative to the rotation of the guide 20 and the middle handle 44. The middle handle 44 being fixed to the guide 20 allows the lower handle 42 to be held in the non-rotatable fashion as the surgeon rotates the middle handle 44 thereby driving the bone anchor 14 into the bone 4. As the bone anchor 14 is being driven into the bone 4, the punch shaft 30, being released from the locked position, is free to linearly move outwardly relative to the bone opening. During this movement, the punch 12 can be released at any time. The snap release feature 37 is easily overcome by the resistance of the bone tissue 4. Alternatively, the punch 12 could, if the tissue 4 is very soft, continue to ride up the punch shaft 30 as it moves outward during the rotation and the driving of the bone anchor 14, such that, when the punch bottoms against the bone anchor 14, it will automatically release from the shaft 30. As shown in FIGS. 27C and 27D, once the bone anchor 14 is flush at the bone surface the surgeon simply pulls back and the snap release feature 27 on the guide holding the bone anchor 14 will similarly release allowing the entire device 10 to be pulled free. The beauty of this inventive device 10 is that the entire drive assembly is pulled free of the punch 12 and anchor 14 in such a fashion that no remnants of the punch driver assembly are left in the body. In this way, when the bone anchor 14 and punch 12 are made of non-metallic material, it is possible that the bone anchor 14 and punch 12 can be delivered in a relatively simple straightforward way wherein the entire drive device 10 excepting the punch 12 and anchor 14 is pulled out free of the patient leaving no metallic materials in the patient.

In almost all other conventional bone anchor delivery systems, the surgeon is required to hold a handle and rotate the device and the entire device rotates as the bone anchor is being positioned into the bone. When this occurs, the surgeon has no ability to either stabilize the device as provided in the present invention and further by being gloved, the surgical gloves have a tendency to wrap about the rotating prior art devices as they are being rotated, if the surgeon is attempting to hold onto the device with his other hand as he is rotating the device to anchor a bone anchor.

With the present invention, the gloved hand of the surgeon is held on a non-rotating leading handle 42 of the multi-part handle 40 as the middle handle 44 and locking knob 46 of the handle 40 are rotated, thereby driving the bone anchor 14. While this is a simple innovation, it is believed significant in that the surgeon can stabilize the bone anchor 14 preventing it from wobbling using two hands; one hand strictly for stabilization as the other hand provides rotation. More importantly, it is designed so that the surgeon's glove does not get wrapped or otherwise pinched into the rotating portions of the device. No other prior art device is known to have such a feature.

Furthermore, to the unique simplicity of the device 10 wherein the punch shaft 30 is made basically of a single stainless steel wire that has a machined leading end 33 sharpened to a point at the tip 35 of the reduced diameter and extends upwardly to an end where the wire is bent and formed to form a locking mechanism bent end 38 that abuts ribs 43, 45 in the upper handle 44. This locking feature being integral to the wire makes it a very low cost structure. Fundamentally, the device 10 is made of a guide 20, a punch shaft 30 and the multi-part handle 40. The handles 42, 44 and 46 are plastic molded parts. This provides for a reasonably low cost, if not very low cost, bone anchor delivery system. The bone anchors 14 themselves can be small plastic components as well. This means that the surgeon will be able to use this device and throw it away if so desired due to its significant simplicity and low-cost construction.

Figure 6B:
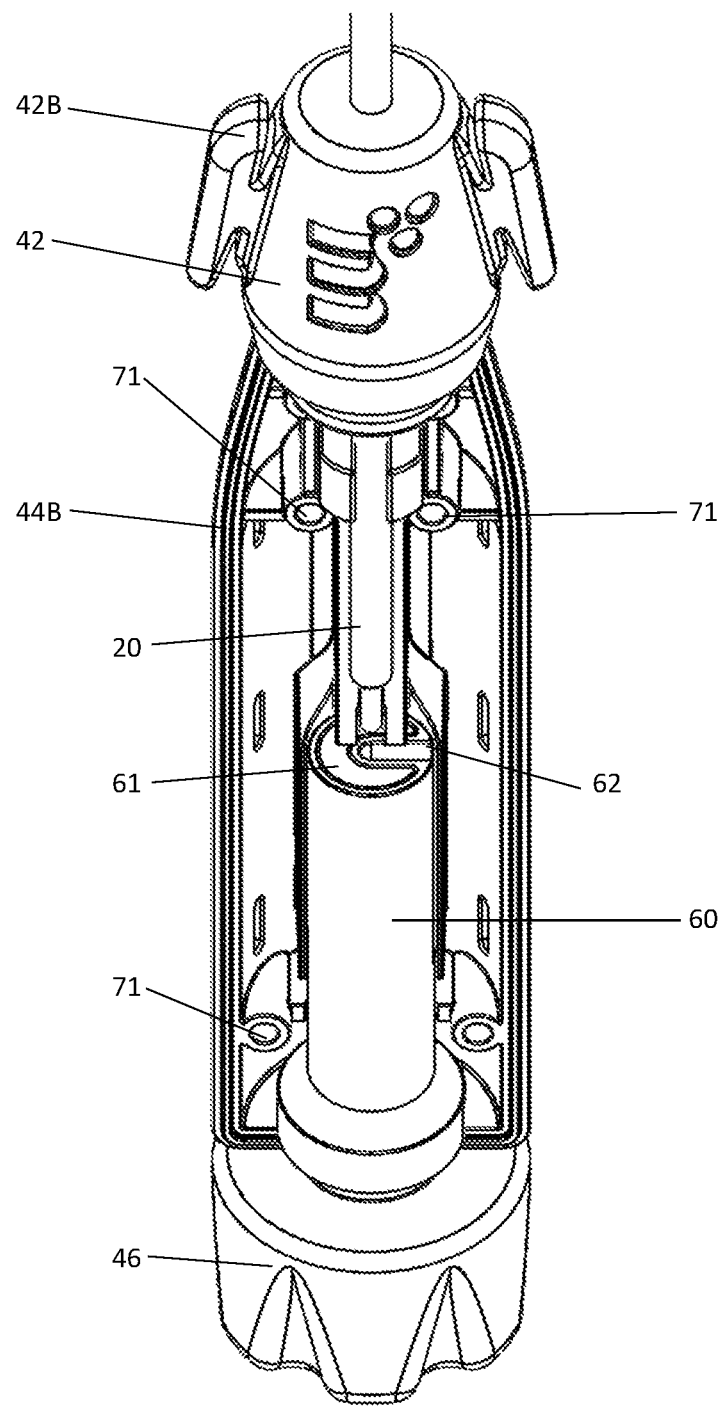
FIG. 6B is a perspective view of the handle showing the opposite half of the middle handle portion and the end of the shaft in the extended, but locked orientation.
Figure 7:
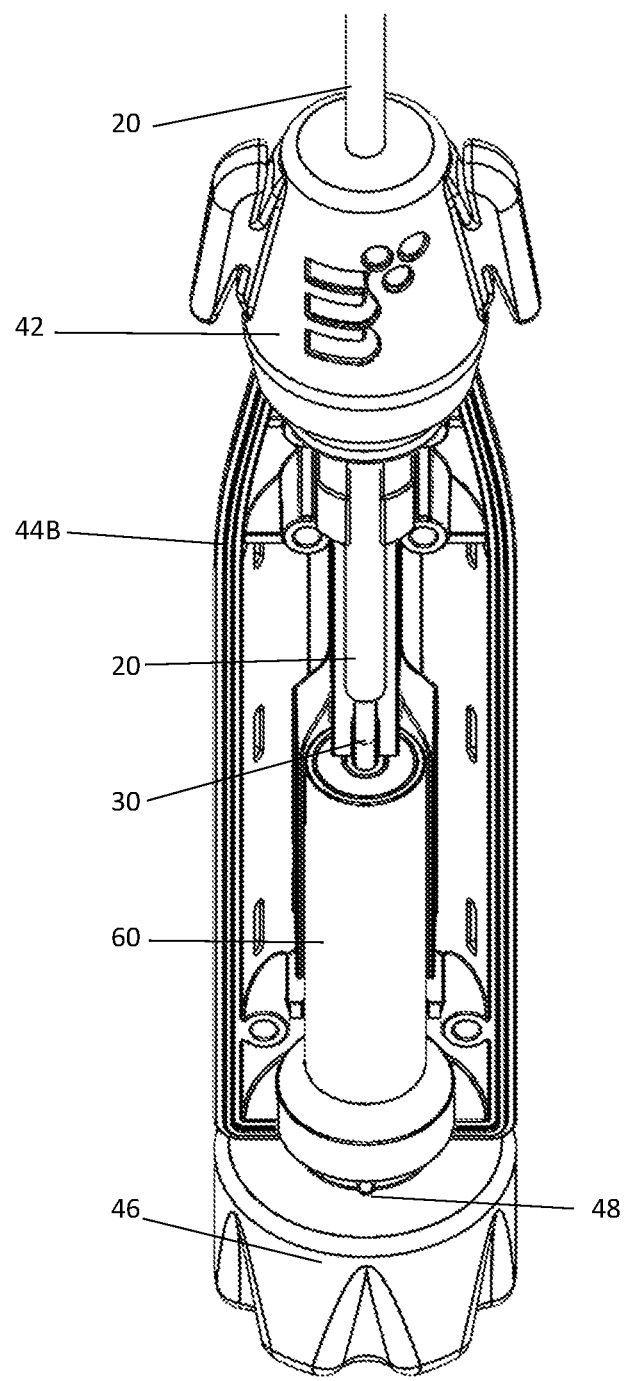
FIG. 7 is the perspective view of FIG. 6B, but with the locking knob rotated to an unlocked orientation with the trailing end of the shaft aligned with the channel to allow the handle to be moved relative to the shaft to an anchor implanting orientation.
Figure 8:
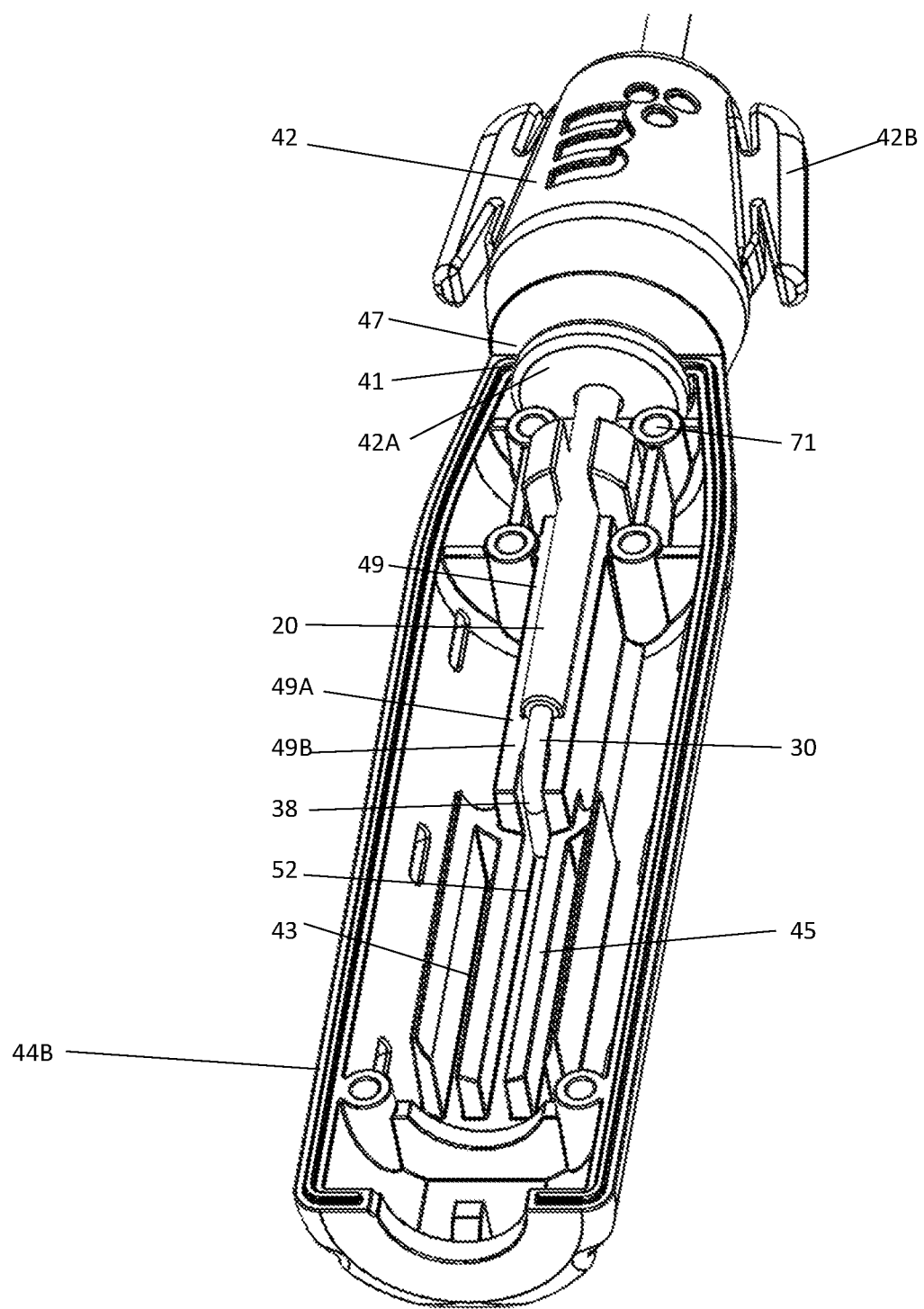
FIG. 8 is a perspective view of the handle of FIG. 7 with the locking knob removed and the trailing end of the shaft aligned with the channel in the middle portion, but prior to moving the handle toward the leading end of the shaft.
Figure 9:
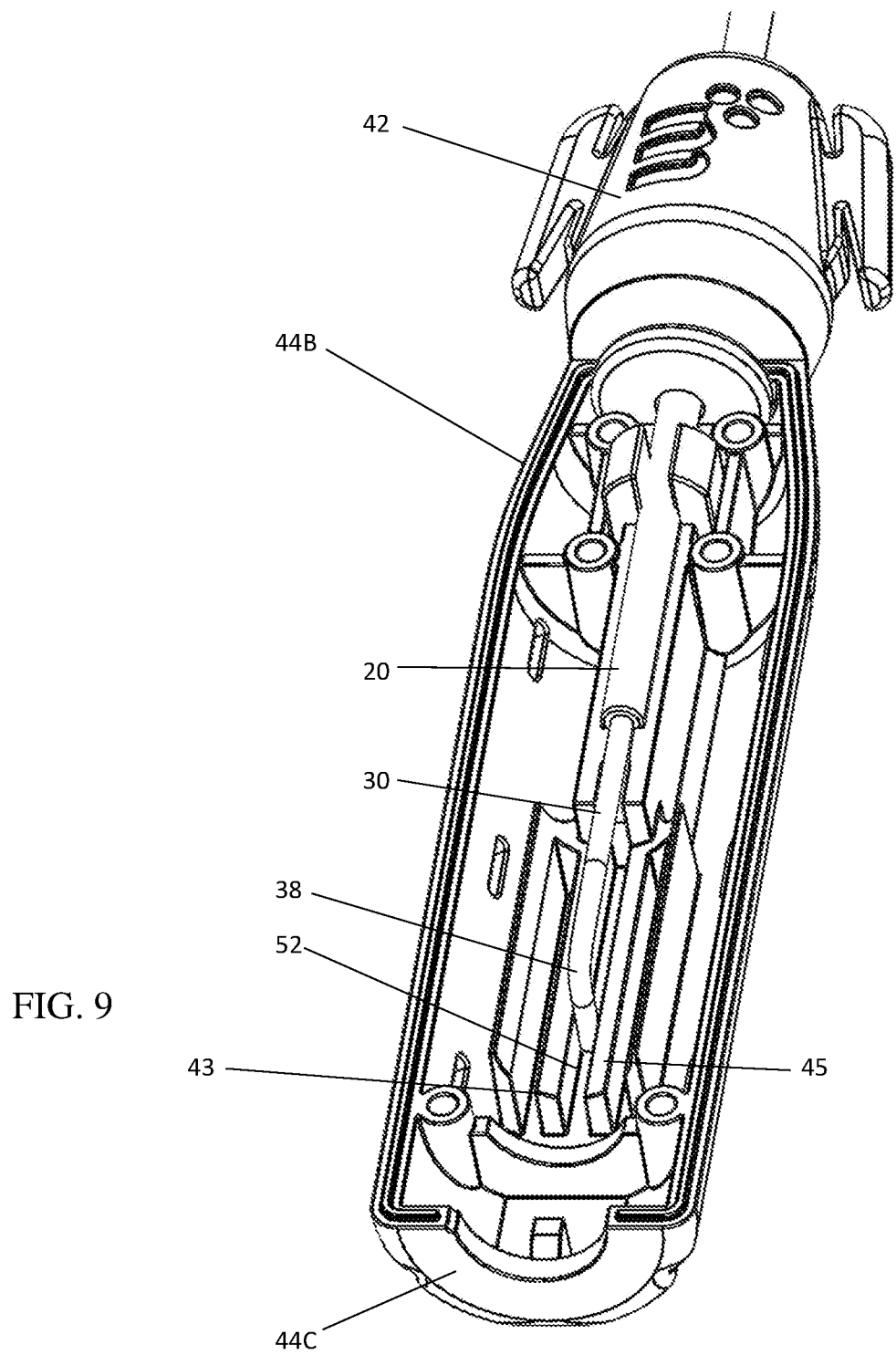
FIG. 9 is the view taken from FIG. 8, but with the handle moved toward the leading end of the shaft as the trailing end slides in the channel.

With reference to FIGS. 6A-26, the multi-piece handle 40 is illustrated in the various figures. With reference to FIG. 6A, the multi-piece handle 40 has the middle handle longitudinal half 44B removed exposing the internal workings of the handle 40. The longitudinal half 44A of the middle handle 44 is attached to the leading end handle 42 and the locking knob 46 as illustrated. As further shown, the guide 20 extends through middle handle 44 and lies within a channel 49 and abuts against a stop 49A, best shown in FIG. 8. The guide 20 is affixed to the handle half 44A as illustrated in such a fashion that the guide 20 is non-rotatably fixed to the middle handle 44 and yet can freely rotate about the leading handle 42. As further shown, the shaft 30 extends further in a narrower channel 49B to the bent end 38. As shown in FIGS. 6A and 6B, the bent end 38 lies in such a way that it is stopped by the cylinder 60 of the locking knob 46 in the illustration. The bent end 38 abuts against the end 61 of the cylinder 60 as illustrated and therefore is in a locked position. When the locking knob 46 is rotated as shown in FIG. 7, the bent end 38 aligns with a channel 62 in the cylinder. In this position, when the locking knob 46 is turned to an unlock position, the bent end 38 of the shaft 30 will be able to slide freely relative to the channel 62 in the cylinder 60 of the locking knob 46. In FIG. 8, the locking knob 46 has been removed and as illustrated, the bent portion 38 of the shaft 30 lies between two ribs 43, 45 that form a channel 52 within the middle handle portion 44. As illustrated in FIGS. 8 and 9, the opposite half 44B of the middle handle 44 is illustrated. As shown in FIG. 6A, the half 44A has pegs 70 that project outwardly and the opposite half 44B has corresponding cylinders 71. As shown, there are 6 of these cylinders 71, 4 near the leading end 42 and 2 at the trailing end. When the cylinders 71 are pushed together with pegs 70 they hold the longitudinal halves 44A, 44B together forming the middle handle 44 of the handle assembly 40. When the assembly 40 is made, the halves 44A, 44B securely hold the leading handle 42 in a groove 47 formed in the leading handle 42 wherein the leading handle 42 circular end 42A has an annular groove 47 that allows the two halves 44A, 44B of the middle handle 44 to encircle it and lock the leading handle 42 into position, but free to rotate relative to the middle handle half 44. The halves 44A, 44B can be adhesively glued, friction fit, head welded or held together by fasteners (not shown) or combinations of this to make the assembled middle handle 44.

FIG. 9 shows the middle handle half 44B with the locking knob 46 removed and illustrates how the shaft 30 and bent end 38 can move relative to the middle handle portion 44B by sliding between the ribs 43, 45 in the channel 52 formed by those ribs.

Figure 10:
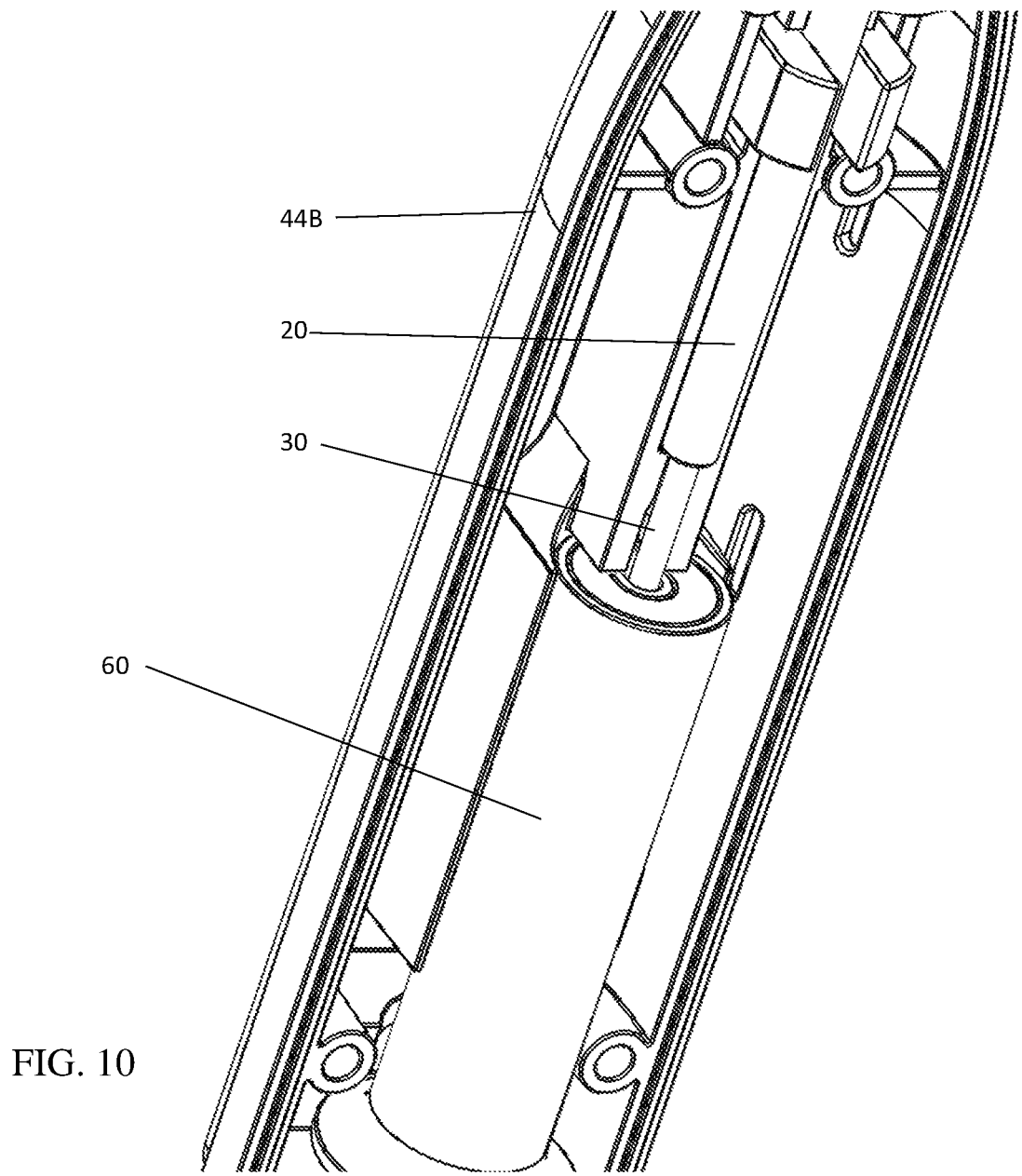
FIG. 10 is the view of FIG. 9, but with the locking knob rotated to the unlocked condition and the trailing end of the shaft in the channel.

An enlarged view of the middle handle half 44B with the locking knob 46 installed is shown in FIG. 10 wherein the shaft 30 is positioned in the cylinder channel 62 of the locking knob 46 illustrating the unlocked position.

Figure 11:
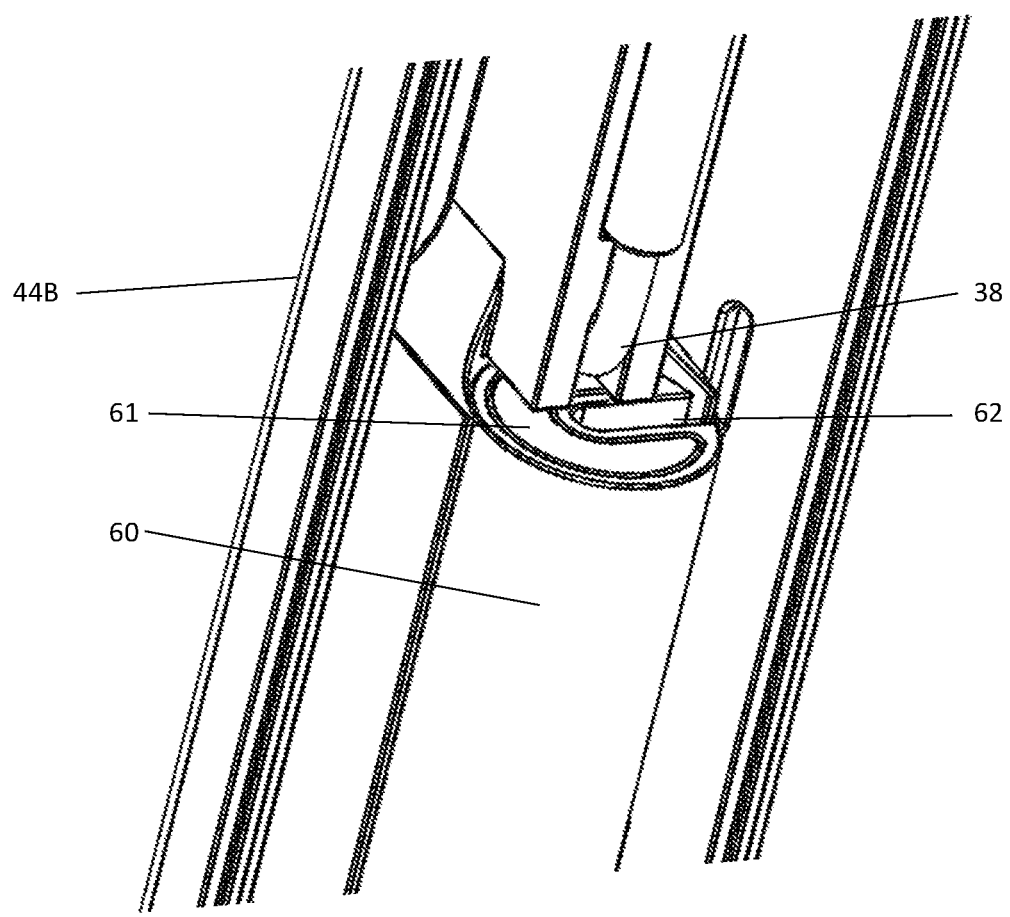
FIG. 11 is an enlarged partial view of the locking knob rotated to the locked position preventing the shaft trailing end from entering the channel.

FIG. 11 is an enlarged view of the middle handle half 44B showing the locked position wherein the cylinder 60 is rotated such that the bent end 38 of the shaft 30 is held in a locked position and cannot be moved relative to the handle 44.

Figure 12:
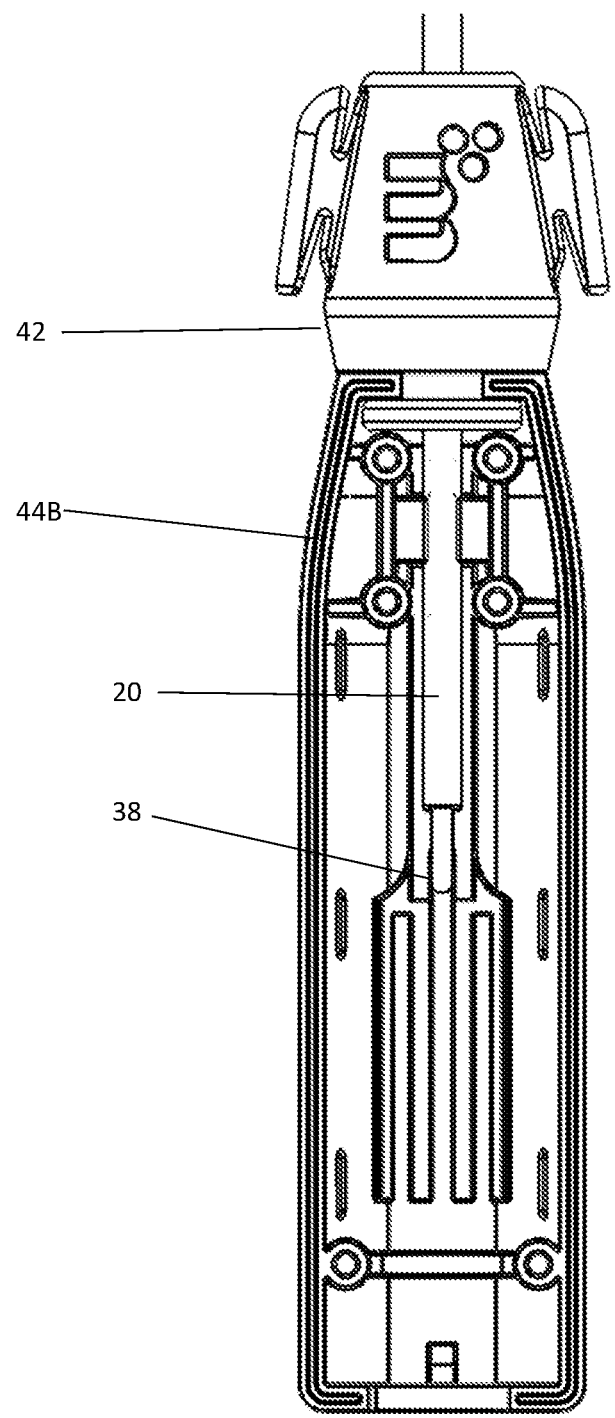
FIG. 12 is a plan view of the handle with the locking knob removed with the shaft trailing end aligned with a channel.

In FIG. 12, the cylinder 60 and locking knob 46 have been removed showing the middle handle 44B in the locked position.

Figure 13:
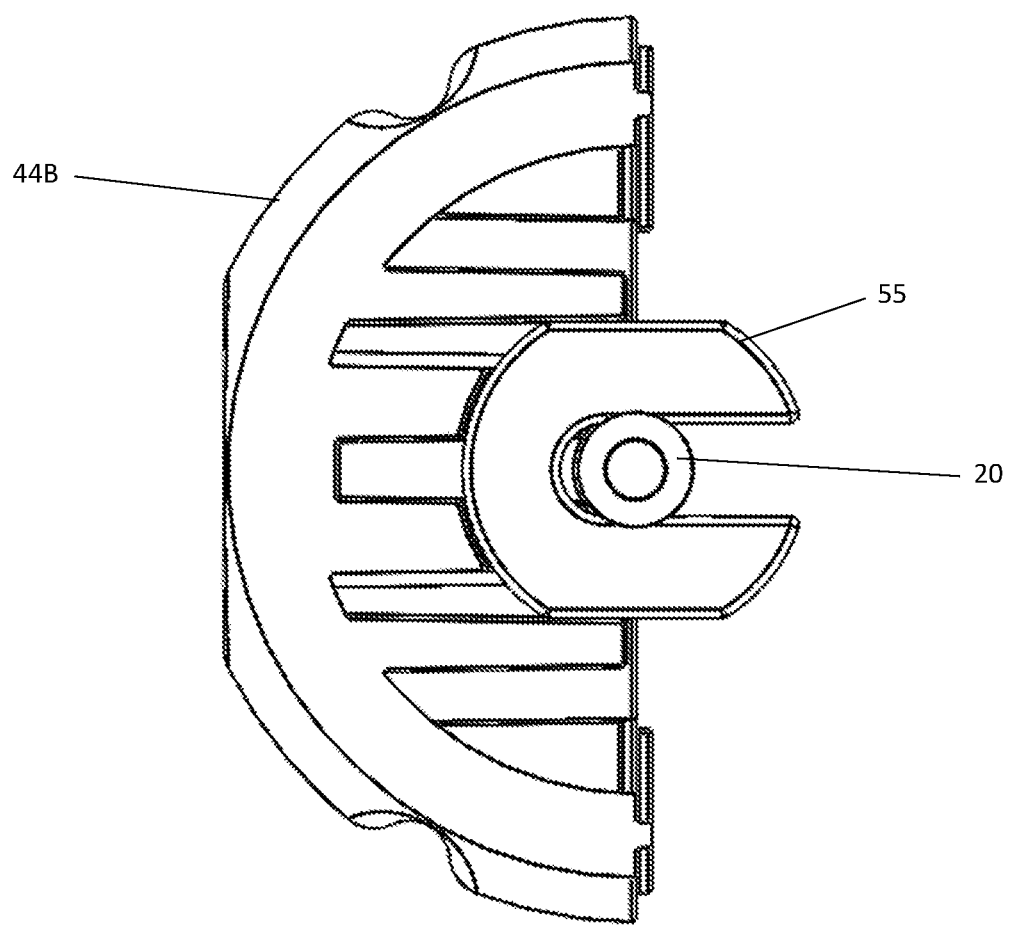
FIG. 13 is a plan view of the handle with the shaft, the locking knob and leading end handle portion removed.
Figure 15:
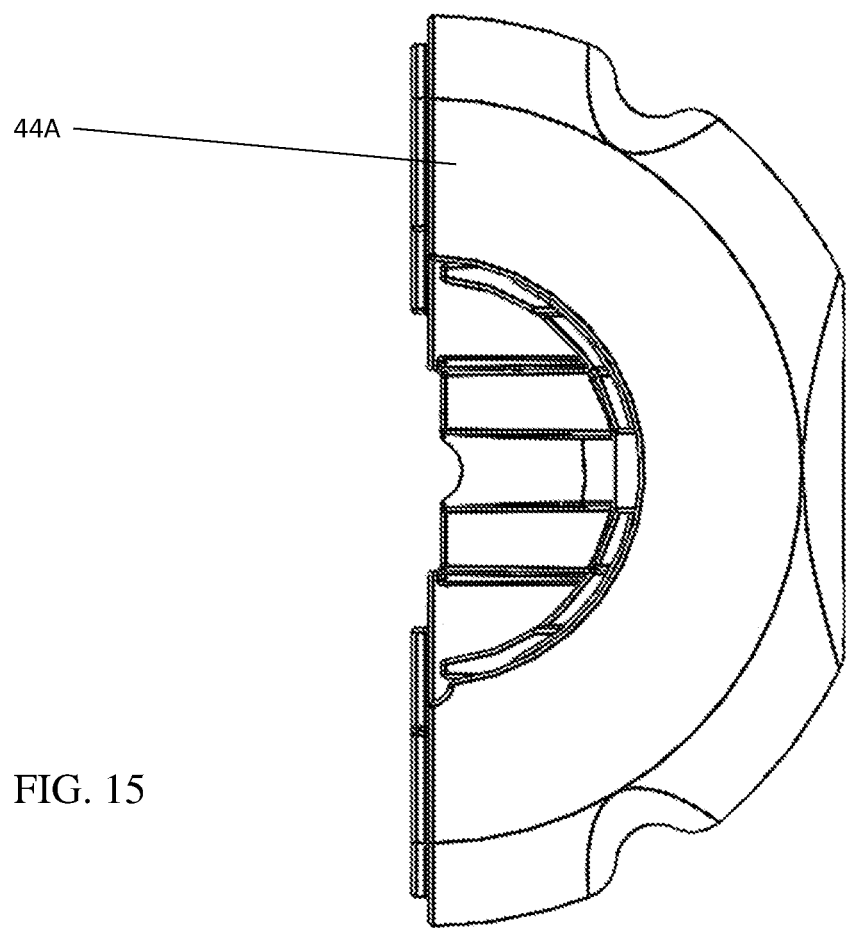
FIG. 15 is an end plan view of the half of the middle portion leading end.

FIG. 13 shows the guide 20 being held in a U shaped portion 55 of the middle handle half 44B. The other middle handle half 44A is shown in FIG. 15.

Figure 14:
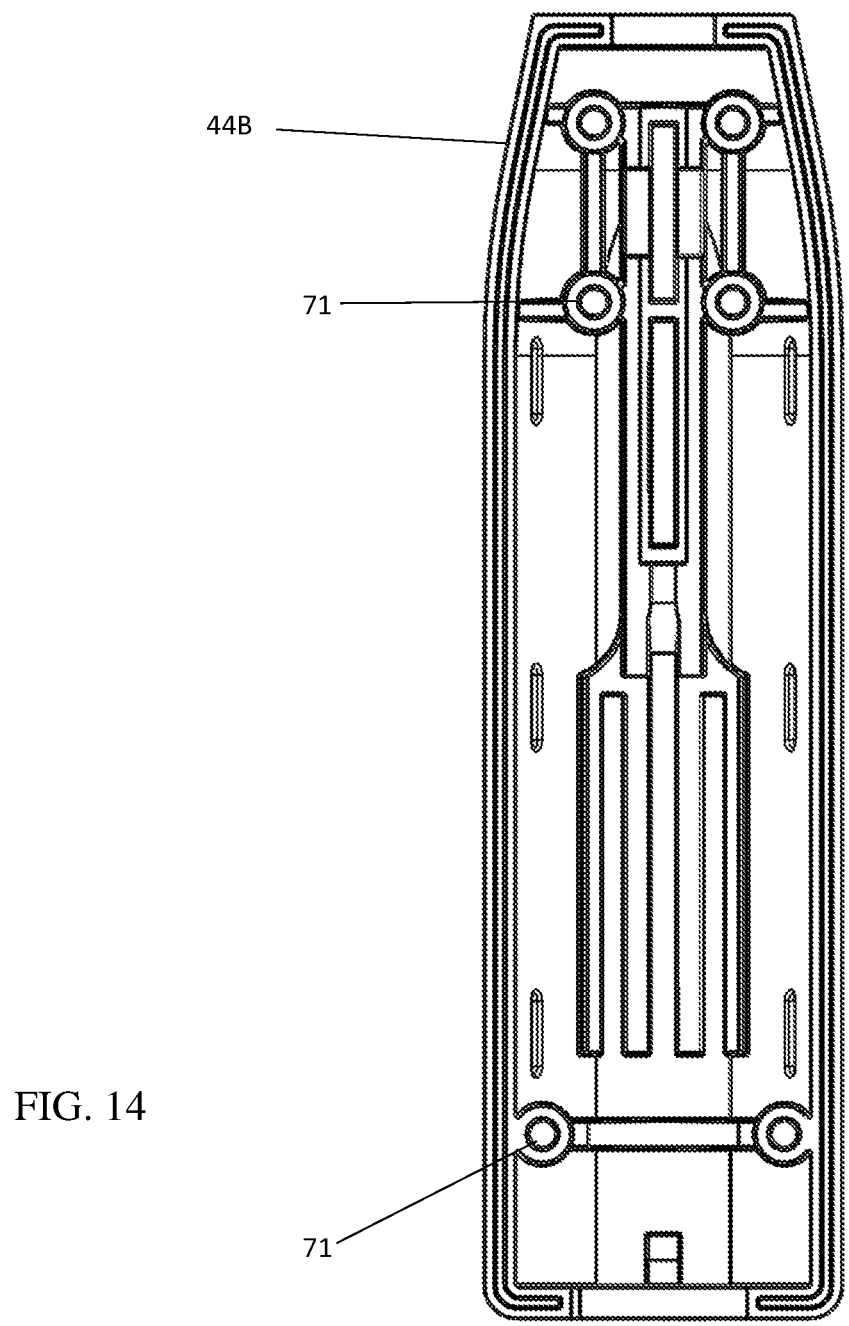
FIG. 14 is a plan view of half of the middle handle portion.

FIG. 14 shows the middle handle portion 44B illustrated in without any components.

Figure 16:
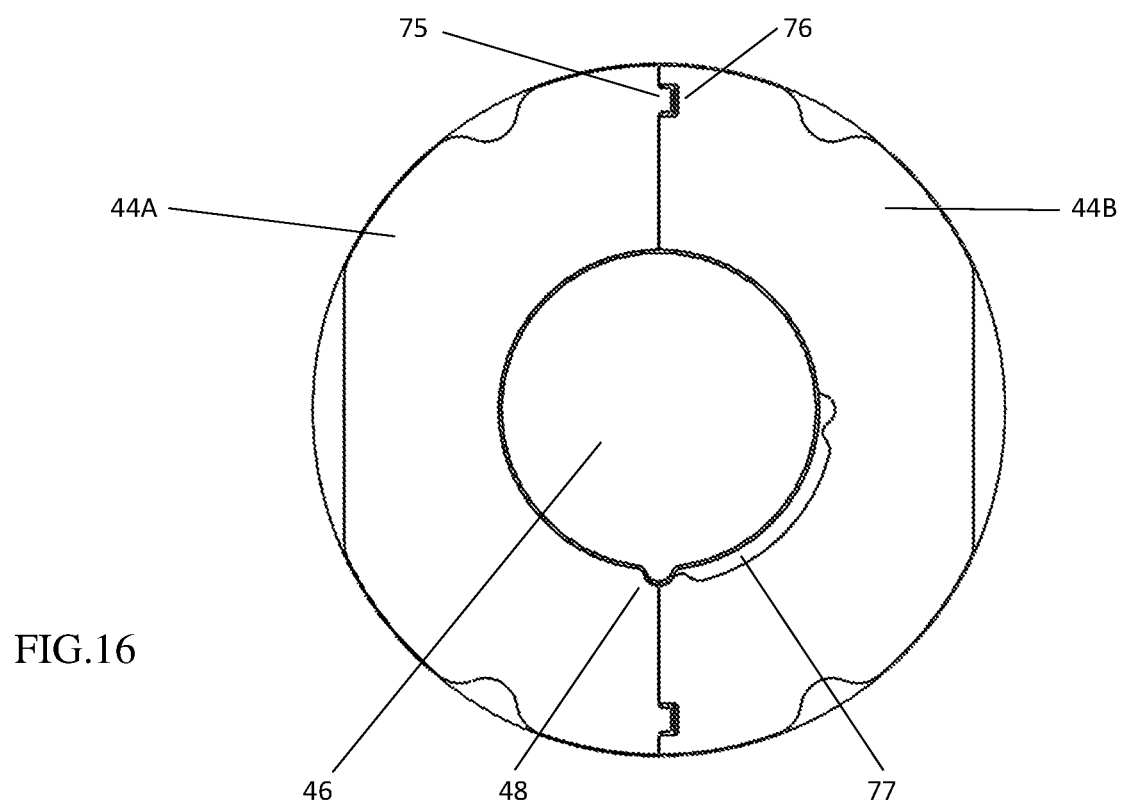
FIG. 16 is an end view of the middle handle portion with both halves joined and illustrating a center opening with a pair of bumps or protrusions at the start of and end of the ¼ turn of the locking knob which has a bump or protrusion, the traversing of the locking knob bump over the middle handle portion bumps provides a tactile feel as the locking knob is moved 90 degrees from a locked orientation to an unlocked position.

FIG. 16 illustrates the two middle handle 44 halves 44A, 44B joined together with raised edge 75 and channel 76 and once so joined encircling a portion of the locking knob 46, it is interesting to note that a recess 77 is in the inner diameter, this recess effectively is illustrated best in FIG. 16.

Figure 17:
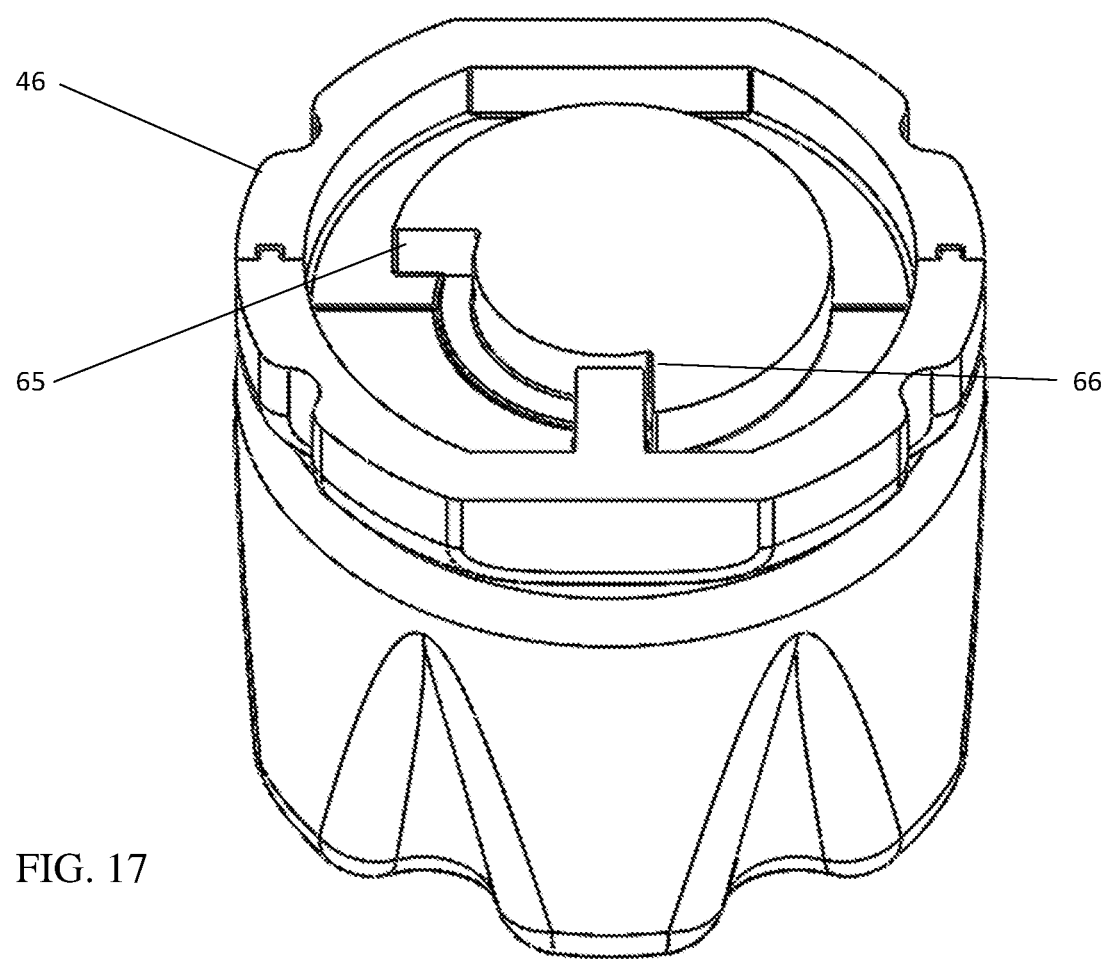
FIG. 17 is a top perspective view of the locking knob showing a ¼ turn cutout with stops.
Figure 18:
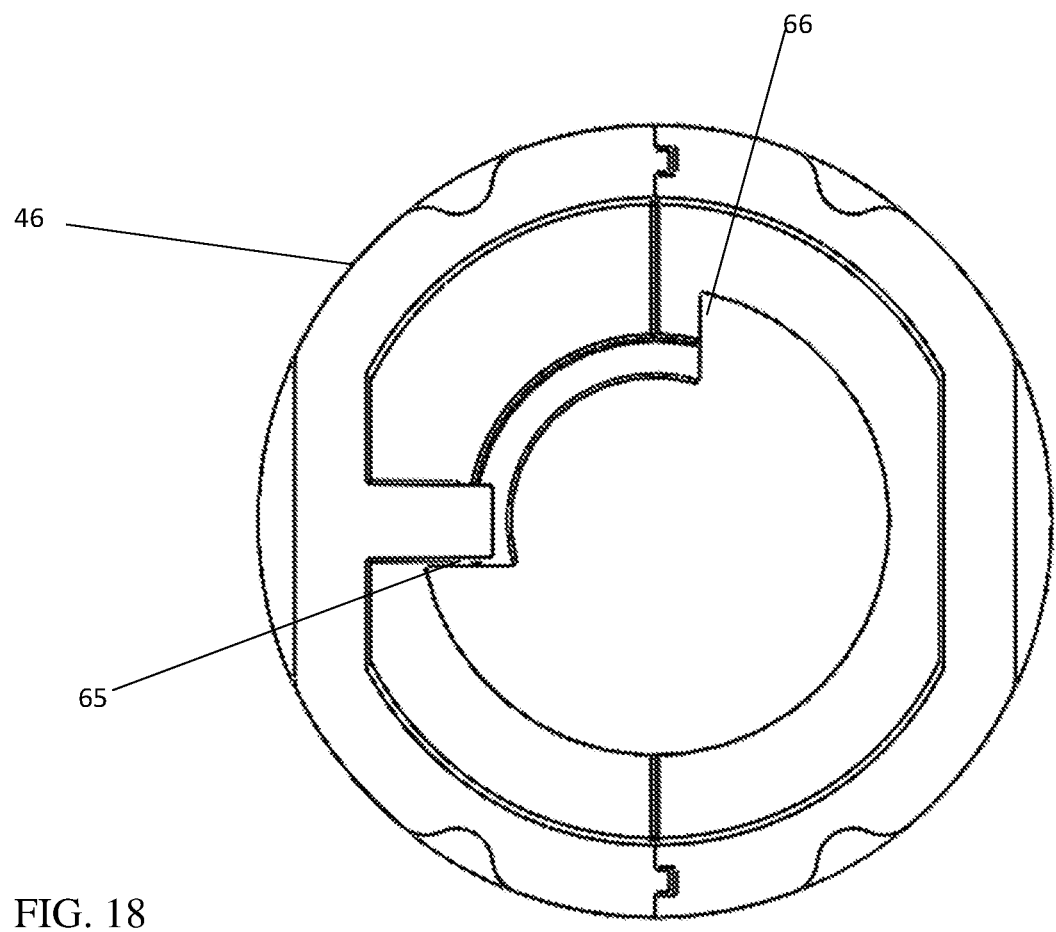
FIG. 18 is a top plan view of the locking knob taken from FIG. 17.

FIG. 17 shows the locking knob 46 wherein the cylinder 60 extends to form the stop 65, 66 such that when the locking knob 46 is only able to turn 90 degrees before abutting against the cylinder. This is also shown in a top view in FIG. 18.

Figure 19:
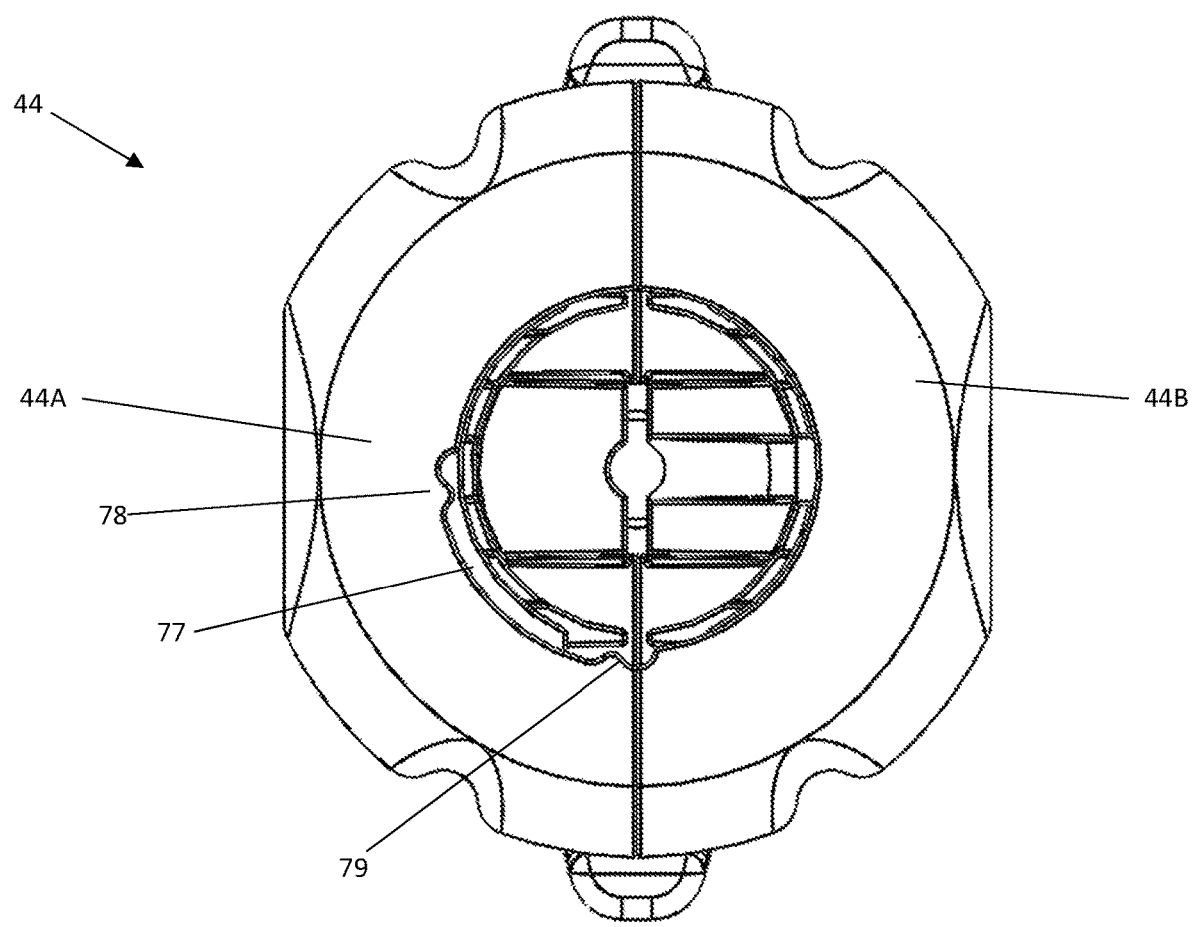
FIG. 19 is a bottom end plan view of the middle handle portion illustrating the tactile feel features.

FIG. 19 illustrates the middle handle portions 44A, 44B from an end view.

Figure 20:
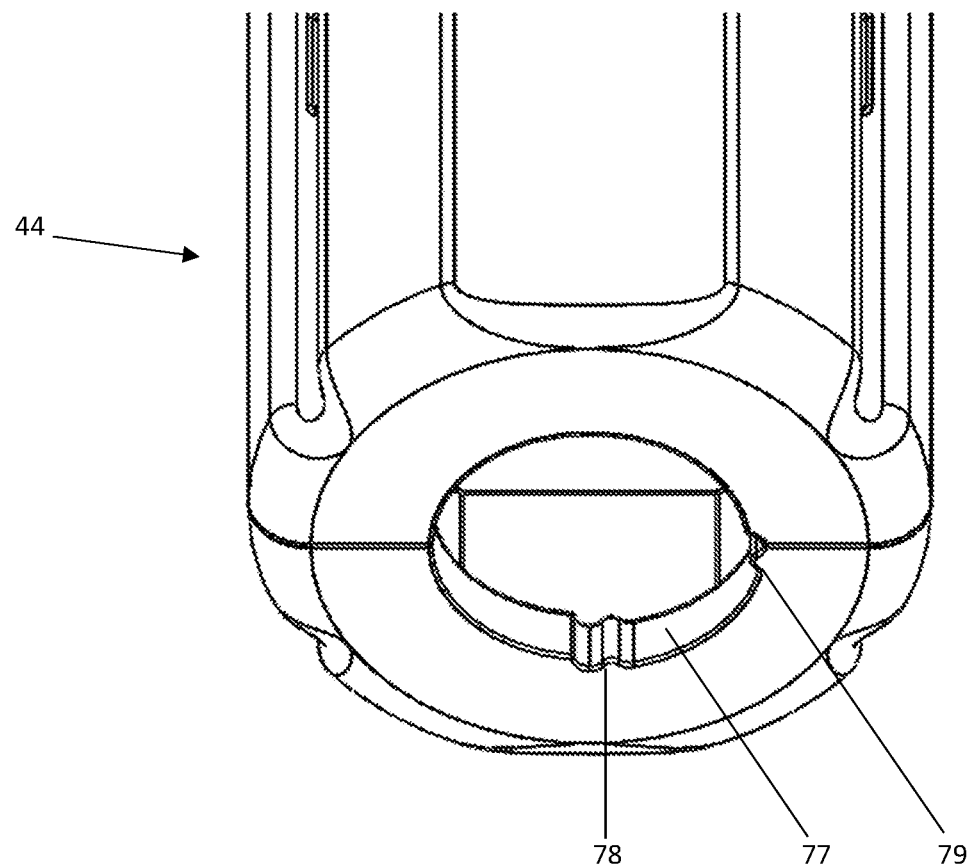
FIG. 20 is a top perspective view of the middle handle portion showing the tactile feel protrusions at the beginning and end of the 90 degree turn region.

FIG. 20 is a perspective view of the middle handle portions 44A, 44B. In this perspective view, the opening is illustrated and better shows the protrusions 78, 79 that extend axially inward from a top surface to an inner surface. These protrusions 78, 79 act as tactile indicators so that when the surgeon turns the locking knob 46, the locking knob 46 has a complimentary bump 48 that is sitting in the recess at the initial stop lock position and that bump 48 must pass over the protrusion 78 in the middle handle 44 and is free to move until the surgeon feels it hit and pass over a second protrusion 79 at which point the middle handle 44 and the locking knob 46 are in the unlocked position. The bump 48 is best shown in FIG. 16. At this point, rotation of the locking knob 46 and the rotation of the middle handle 44 can be performed as the two parts will move in unison being locked together as they have reached the full unlocked position allowing the shaft 30 to be able to move freely relative to the handles. In the unlocked position, as previously discussed, the handle and locking knob 46 are free to move relative to the shaft 30 towards the leading end 42 where the anchor and tip are positioned. As the handles are rotated, the anchor threadingly engages the bone and is therefore held in position.

Figure 21:
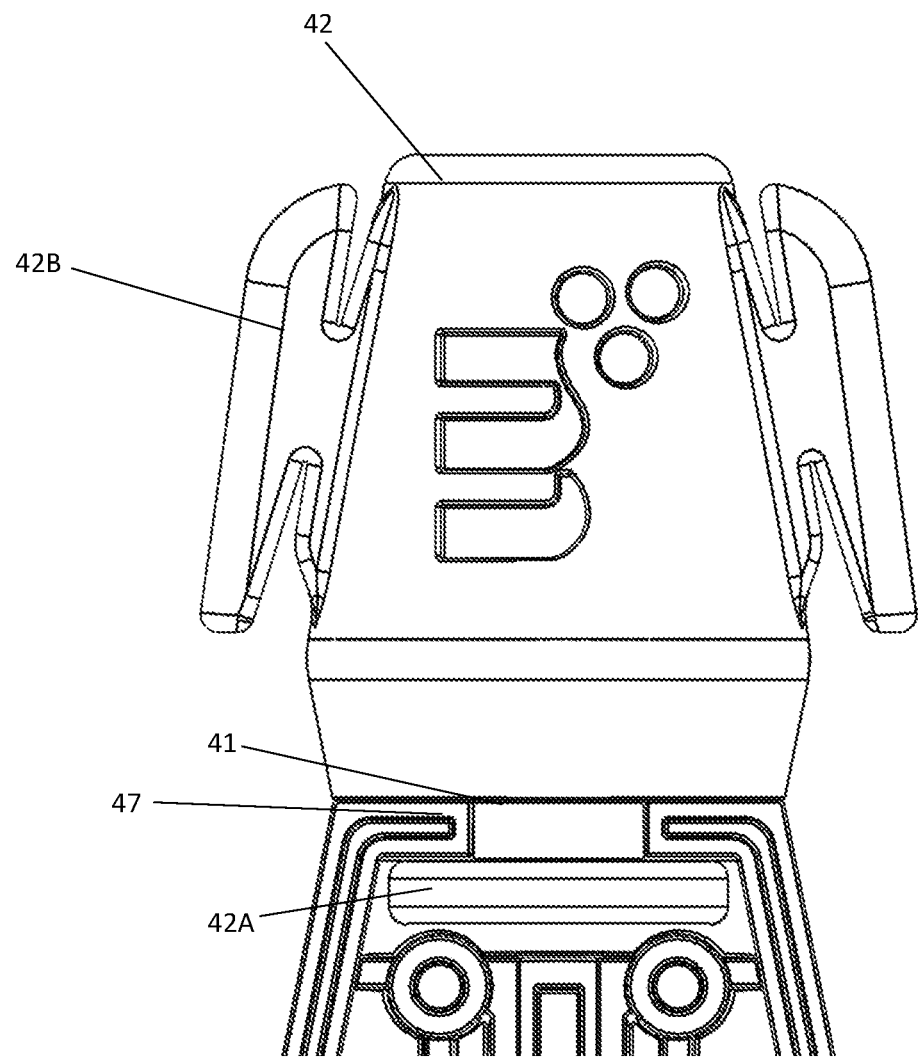
FIG. 21 is an enlarged side view of the leading end handle portion and a half portion of the middle handle attached thereto.

FIG. 21 illustrates an enlarged view of the leading end 42. The enlarged view shows the leading end 42 having a pair of appendages 42B, one on each side. These appendages 42B are provided such that a surgeon can loop sutures around these appendages 42B if so desired. As further shown, the leading end 42 has a cylindrical end 47 extending to an enlarged annular disc 42A which is captively held in the two middle half portions 44A, 44B. This is clearly shown in FIG. 21 wherein one half 44A of the middle portion 44 is removed so that one can visualize how the leading end 42 is held in position.

Figure 22:
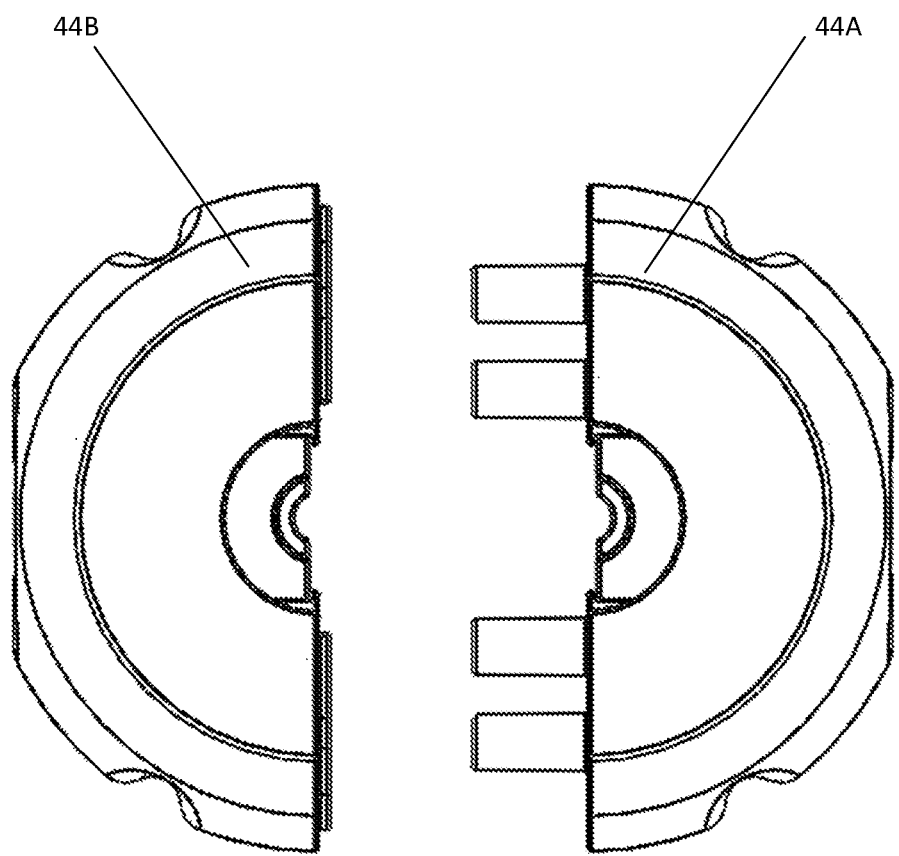
FIG. 22 shows an end plan view of the two halves of the middle handle prior to assembly.
Figure 23:
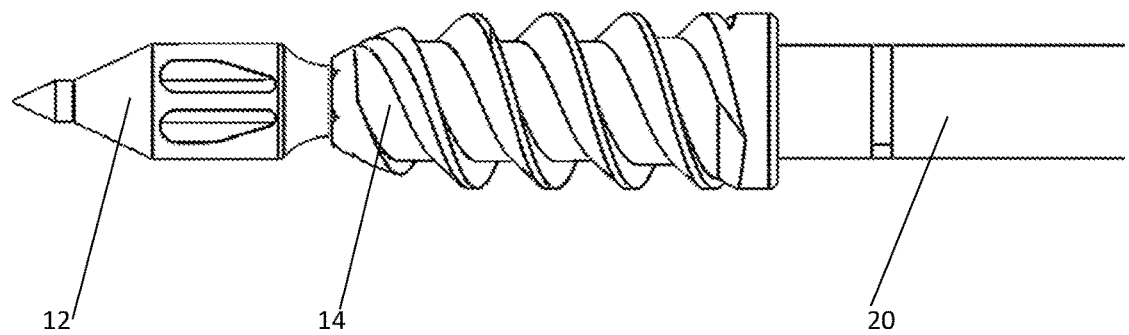
FIG. 23 shows the side plan view of a portion of the guide, the anchor and the tip on the shaft with the anchor and tip in the implanted position.

FIG. 22 is a further illustration of the middle handle 44 having the two halves 44A, 44B separated, but aligned to be joined together to make the completed handle assembly 40.

FIG. 23 is again a view of the punch 12 and threaded anchor 14 mounted on the shaft 30 held on the guide 20.

Figure 24:
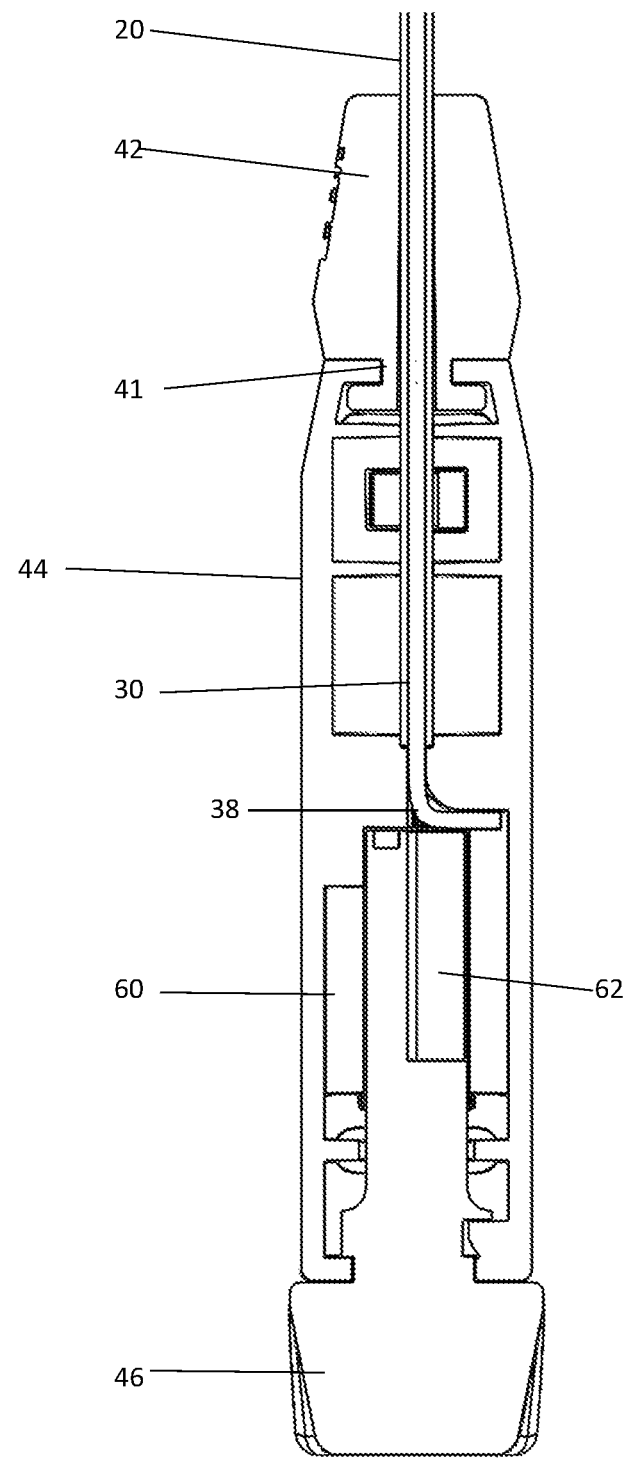
FIG. 24 is a cross-sectional view of the handle in the unlocked position, but the shaft in extended orientation prior to the handle moving.

FIG. 24 shows the internal cross-sectional view of the handle assembly 40 with the bent end 38 held in an unlocked position aligned with the channel 62, but not moved linearly.

Figure 25:
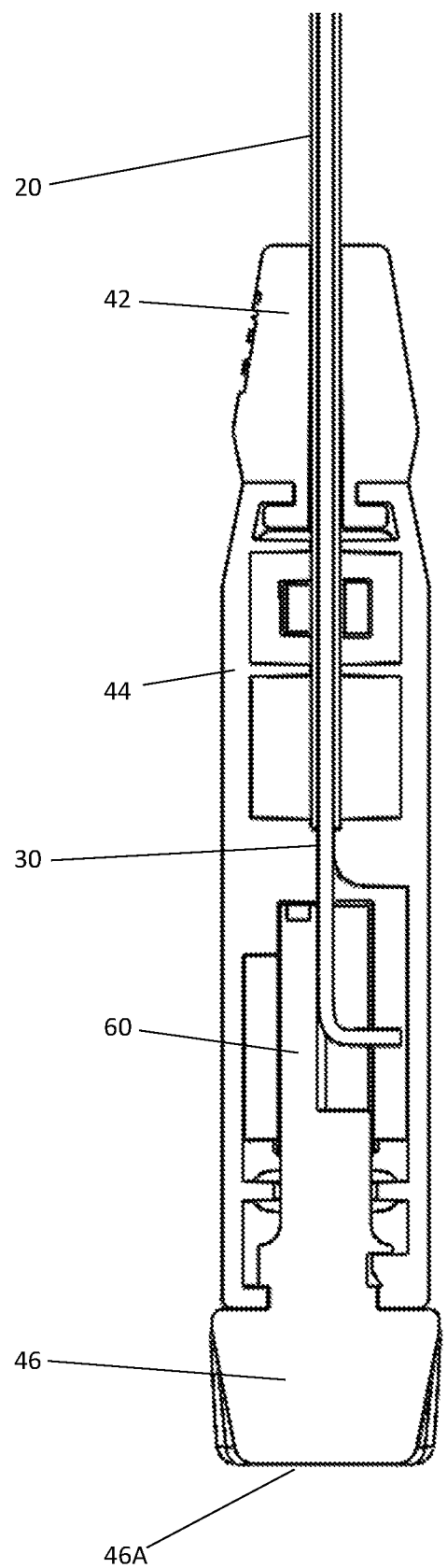
FIG. 25 is a side cross-sectional view showing the handle being driven toward the leading end of the shaft.

FIG. 25 shows the locking knob 46 has been rotated in such a fashion that the bent end 38 is allowed to slide within the channel 62 of the cylinder 60 of the locking knob 46. In this position is where the anchor can then be threaded into the bone.

Figure 26:
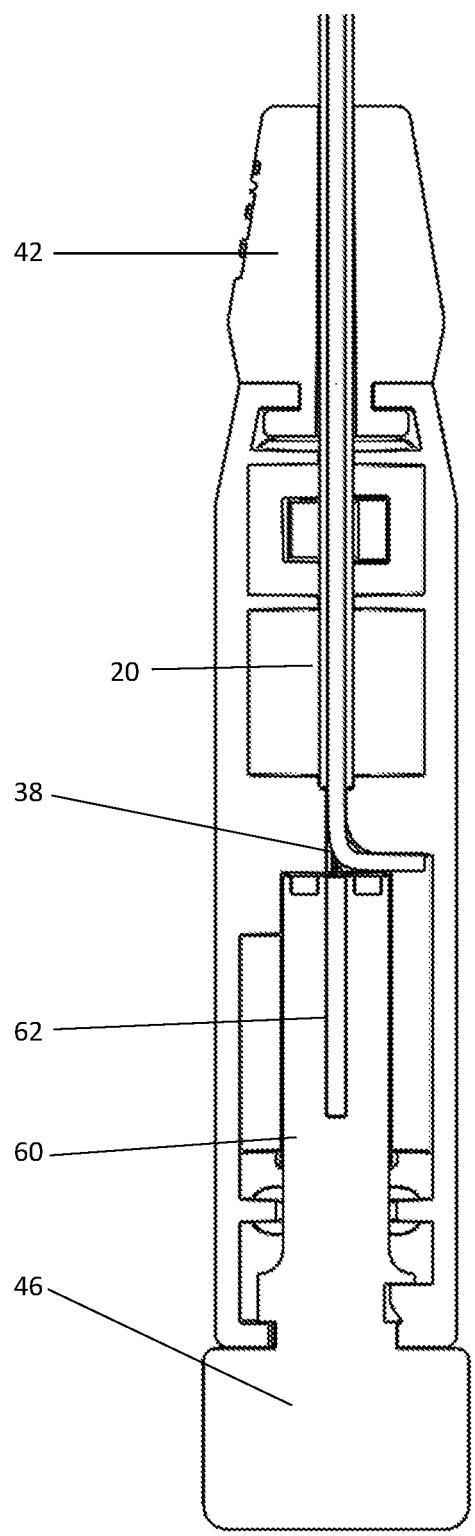
FIG. 26 is a cross-sectional view with the locking knob in a locked position with the shaft held in extended position locked in place.

FIG. 26 is a view similar to FIG. 24, but with the cylinder 60 showing the channel 62 moved in the locked position wherein the shaft 30 cannot move linearly.

All of these figures provide a unique multi-piece handle 40 which provides a simplified way of locking and unlocking the L shaped bent end 38 of the shaft 30 to allow the surgeon a more easily and ergonomically more efficient way of delivering a punch into a bone structure with the sutures attached and thereafter threading the anchor into position.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A bone anchor delivery system device comprising:
a retractable punch driver assembly, the punch driver assembly having a retractable punch shaft and a guide for receiving the retractable punch shaft, the guide being rotatable relative to the punch shaft and the shaft having an extended length with bone penetrating tip at a first end, and a bent end for locking the retractable punch shaft from linear movement and rotational movement relative to the guide at an opposite second end;
a multi-piece handle assembly, the handle assembly having a leading handle rotatable about the guide and a middle handle portion fixed to the guide and a locking knob configured to prevent linear movement of the retractable punch and wherein the middle handle is rotatable independent of said leading handle, the middle handle has a slot to receive the bent end to allow linear movement of the retractable punch shaft; and
wherein the punch shaft is a rod or wire and the bent end is integrally formed as part of the rod or wire at the second end by a bending of the punch shaft to fit into the slot of the middle handle and a cylinder of the locking knob has an end locking the punch shaft in place linearly.

2. The bone anchor delivery system device of claim 1 wherein the bent end of the shaft is L shaped at the second end.

3. The bone anchor delivery system device of claim 1 wherein the middle handle has two longitudinal halves, each half having a leading end and a trailing end, each end has a semicircular opening and when the halves are joined the openings form a circular opening, the leading end configured to rotatably hold the leading handle and the trailing end opening configured to receive the locking knob.

4. The bone anchor delivery system device of claim 1 wherein the bent end of the shaft when placed in a first half of the middle handle lies in between two ribs, the ribs extending longitudinally forming the slot for allowing linear movement.

5. The bone anchor delivery system device of claim 1 wherein the leading handle has a pair of appendages for wrapping lengths of sutures about.

6. The bone anchor delivery system device of claim 1 wherein the locking knob has a bump aligned with the trailing end opening of the open end of the middle handle, the open end has a pair of linear extending protrusions, a first protrusion is at a locked position, the second protrusion is at an unlocked position, and when the bump passes each protrusion as the locking knob rotates relative to the middle handle, a tactile feel indication occurs.

7. The bone anchor delivery system device of claim 1 wherein the locking knob moves from the lock position to the unlock position by a quarter turn rotation.

8. The bone anchor delivery system device of claim 7 wherein the rotation of the locking knob to the unlock position couples the middle handle and the locking knob so rotation of either rotates both.

9. The bone anchor delivery system device of claim 8 wherein the quarter turn rotation to the unlock position is directionally clockwise.

10. The bone anchor delivery system device of claim 9 wherein continued rotation clockwise threads the anchor in bone as the shaft moves towards a retracted position in the channel.

11. The bone anchor delivery system device of claim 1 wherein the retractable punch shaft has a reduced diameter end extending from the tip toward a shoulder stop for receiving a releasable punch, the releasable punch having a hollow opening for receiving the reduced diameter end and bone penetration tip at the first end profiled to be complimentary to the tip and an opposite second end for abutting the shoulder stop of the punch shaft.

12. The bone anchor delivery system device of claim 11 wherein the reduced diameter end of the punch shaft and the punch have a snap lock feature to hold the punch, the snap lock feature allows for rotational movement of the punch relative to the punch shaft.

13. The bone anchor delivery system device of claim 11 wherein the releasable punch has a plurality of openings for threading one or more sutures.

14. The bone anchor delivery system device of claim 13 wherein the releasable punch openings are one or more pairs of slots sized to receive a plurality of sutures.

15. The bone anchor delivery system device of claim 13 further comprises a releasable threaded bone anchor, the threaded bone anchor being hollow having an opening for attachment onto the guide, the bone anchor extending from a first leading end to an opposite second end abutting the guide.

16. The bone anchor delivery system device of claim 15 wherein the guide has a reduced end having a snap lock feature and the bone anchor has a complimentary releasable lock for holding the bone anchor to the guide.

17. The bone anchor delivery system device of claim 16 wherein rotation of the middle handle portion after the locking knob is unlocked allows the bone anchor to be driven into a bone opening formed by the punch.

18. The bone anchor delivery system device of claim 17 wherein the punch is released from the punch shaft end by withdrawing of the punch shaft and abutting the leading end of the driven bone anchor.

19. The bone anchor delivery system device of claim 18 wherein the release of the initial retractable punch assembly occurs by pulling past the snap lock feature in the guide and the bone anchor.

20. The bone anchor delivery system device of claim 17 wherein the leading handle provides a non-rotatable hand grip for stabilizing the device as the middle handle portion is rotated.

21. The bone anchor delivery system device of claim 16 wherein the punch shaft extends past the guide and the leading end of the bone anchor when the bone anchor is attached and abutted to the guide at the second end by a length L, wherein L is at least equal to the length of the bone anchor and wherein in the use of the anchor delivery system device the punch tip penetrates the bone creating an opening extending to a depth wherein the bone anchor is positioned adjacent above the bone opening.

22. The bone anchor delivery system device of claim 11 wherein said locking knob has an impact end for impacting the handle assembly to drive the punch through bone.

23. The bone anchor delivery system device of claim 11 wherein the unlocked position allows the punch shaft to move linearly in an elongated slotted opening in the middle portion and the channel of the cylinder of the locking shaft to retract the punch shaft.

24. The bone anchor delivery system device of claim 12 wherein the punch is non-metal.

25. The bone anchor delivery system device of claim 12 wherein the punch is made of synthetic or natural non-metal material.

26. The bone anchor delivery system device of claim 12 wherein the punch is made of a plastic material.

27. The bone anchor delivery system device of claim 26 wherein the plastic material is PEEK (polyether ether ketone).

28. The bone anchor delivery system device of claim 12 wherein the punch is made of a bioabsorbable material.

29. The bone anchor delivery system device of claim 12 wherein the anchor is made of a hardened biological material composition.

30. The bone anchor delivery system device of claim 12 wherein the bone anchor is non-metal.

31. The bone anchor delivery system device of claim 12 wherein the bone anchor is made of synthetic or natural non-metal material.

32. The bone anchor delivery system device of claim 12 wherein the bone anchor is made of a plastic material.

33. The bone anchor delivery system device of claim 12 wherein the bone anchor is made of a bioabsorbable material.

34. The bone anchor delivery system device of claim 12 wherein the bone anchor is made of cortical bone.

* * * * *